US010822624B2

(12) United States Patent
Scrutton et al.

(10) Patent No.: US 10,822,624 B2
(45) Date of Patent: *Nov. 3, 2020

(54) COMPOSITIONS AND METHODS FOR RECOMBINANT BIOSYNTHESIS OF PROPANE

(71) Applicant: C3 Bio-Technologies Limited, Lancaster (GB)

(72) Inventors: Nigel Scrutton, Cheshire (GB); Patrik Jones, Bromley (GB); Navya Menon, Manchester (GB)

(73) Assignee: C3 BIO-TECHNOLOGIES LIMITED, Lancaster (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/405,089

(22) Filed: May 7, 2019

(65) Prior Publication Data

US 2019/0323040 A1 Oct. 24, 2019

Related U.S. Application Data

(63) Continuation of application No. 15/421,861, filed on Feb. 1, 2017, now Pat. No. 10,337,032.

(60) Provisional application No. 62/289,517, filed on Feb. 1, 2016.

(51) Int. Cl.

| C12P 5/02 | (2006.01) |
|---|---|
| C12N 9/10 | (2006.01) |
| C12N 9/88 | (2006.01) |
| C12N 9/12 | (2006.01) |
| C12N 9/02 | (2006.01) |
| C12N 9/16 | (2006.01) |
| C12N 9/04 | (2006.01) |
| C12N 15/52 | (2006.01) |
| C12P 7/16 | (2006.01) |

(52) U.S. Cl.
CPC .............. *C12P 5/02* (2013.01); *C12N 9/001* (2013.01); *C12N 9/0006* (2013.01); *C12N 9/0008* (2013.01); *C12N 9/1029* (2013.01); *C12N 9/1288* (2013.01); *C12N 9/16* (2013.01); *C12N 9/88* (2013.01); *C12N 15/52* (2013.01); *C12P 7/16* (2013.01); *C12Y 101/01001* (2013.01); *C12Y 101/01021* (2013.01); *C12Y 101/01157* (2013.01); *C12Y 102/99006* (2013.01); *C12Y 103/01038* (2013.01); *C12Y 203/01009* (2013.01); *C12Y 203/01194* (2013.01); *C12Y 207/08007* (2013.01); *C12Y 301/0202* (2013.01); *C12Y 401/99005* (2013.01); *C12Y 402/01055* (2013.01)

(58) Field of Classification Search
None
See application file for complete search history.

(56) References Cited

U.S. PATENT DOCUMENTS

| 5,585,089 A | 12/1996 | Queen et al. |
| 5,721,109 A | 2/1998 | Yano et al. |
| 2007/0054335 A1 | 3/2007 | Esfandiari et al. |

FOREIGN PATENT DOCUMENTS

| JP | H07248329 A | 9/1995 |
| WO | 9839025 A2 | 9/1998 |
| WO | 2005116654 A1 | 12/2005 |
| WO | 2010086667 A2 | 8/2010 |
| WO | 2012131394 A1 | 10/2012 |
| WO | 2013186679 A1 | 12/2013 |

OTHER PUBLICATIONS

GB Search Report for GB Application No. GB1514411.6 dated May 26, 2017, 4 pages.
Kallio et al., "An engineered pathway for the biosynthesis of renewable propane," Nature Communications, dated Sep. 2, 2014, 8 pages.
Menon et al., "A microbial platform for renewable propane synthesis based on a fermentative butanol pathway," Biotechnology for Biofuels, (2015), 8:61, 12 pages.
Akhtar et al., "Carboxylic acid reductase is a versatile enzyme for the conversion of fatty acids into fuels and chemical commodities," PNAS, dated Jan. 2, 2013, vol. 110, No. 1, pp. 87-92.
Atsumi S. et al., "Direct photosynthetic recycling of carbon dioxide to isobutyraldehyde," Nat Biotechnol., Dec. 2009, 27(12):1177-1180. Abstract provided.
Bond-Watts BB et al., "Enzyme mechanism as a kinetic control element for designing synthetic biofuel pathways," Nat Chem Biol., Apr. 2011, 7(4):222-227. Abstract provided.
Davis et al., "Inhibition of *Escherichia coli* Aceytl Coenzyme A Carboxylase by Acyl-Acyl Carrier Protein," Journal of Bacteriology, Feb. 2001, vol. 183, No. 4, 1499-1503.
Dellomonaco C. et al., "Engineered reversal of the β-oxidation cycle for the synthesis of fuels and checmicals," Nature, Aug. 10, 2011, 476(7360):355-359. Abstract provided.
Howard et al., "Sythesis of customized petroleum-replica fuel molecules by targeted modification of free fatty acid pools in *Escherichia coli*," PNAS, May 7, 2013, vol. 110, No. 19, 7636-7641.
James et al., "Expression of *Two Escherichia coli* Acetyl-CoA Carboxylase Subunits Is Autoregulated," The Journal of Biological Chemistry, (2004), vol. 279, No. 4, 2520-2527.
Köhler et al., "Deruvation of specific antibody-producing tissue culture and tumor lines by cell fusion," Eur J Immunol., Jul. 6, 1976, (7):511-519. Abstract Provided.

(Continued)

*Primary Examiner* — Kagnew H Gebreyesus
(74) *Attorney, Agent, or Firm* — Hoffman Warnick LLC

(57) ABSTRACT

Provided are genetically engineered microorganism that catalyze the synthesis of propane and/or butanol from a suitable substrate such as glucose. Also provided are methods of engineering said genetically engineered microorganism and methods of producing propane and/or butanol using the genetically engineered microorganism.

20 Claims, 12 Drawing Sheets

Specification includes a Sequence Listing.

(56) References Cited

OTHER PUBLICATIONS

Lan et al., "ATP drives direct photosynthetic production of 1-butanol in cyanobacteria," PNAS, Apr. 17, 2012, vol. 109, No. 16, 6018-6023.

Pásztor et al., "A Synthetic O2-Tolerant Butanol Pathway Exploiting Native Fatty Acid Biosynthesis in *Escherichia coli*," Biotechnol. Bioeng., 2015; 112: 120-128.

Riechmann et al., "Reshaping human antibodies for therapy," Nature, Mar. 24, 1988, 332(6162): 323-327. Abstract provided.

Rodriguez et al., "Toward aldehyde and alkane production by removing aldehyde reductase activity in *Escherichia coli*," Metab Eng., Sep. 2014, 25: 227-237.

Schirmer et al., "Microbial biosynthesis of alkanes," Science, Jul. 30, 2010, 329(5991): 559-562. Abstract provided.

El et al., "Metabolic engineering of cyanobacteria for 1-butanol production from carbon dioxide," Metab. Eng., Jul. 2011, 13(4): 353-363, Abstract Provided.

Lan et al., "Oxygen-tolerant coenzyme A-acylating aldehyde dehydrogenase facilitates efficient photosynthetic n-butanol biosynthesis in cyanobacteria," Energy Environ. Sci, (2013), 6, 2672-2681. Abstract provided.

International Preliminary Report on Patentability for corresponding PCT Application No. PCT/GB2015/052340, dated Feb. 23, 2017, 6 pages.

Nawab et al., "Genetic engineering of non-native hosts for 1-butanol production and its challenges: a review," Microbial Cell Factories 19:79 (2020), 16 pages.

Kunjapur et al., "Microbial Engineering for Aldehyde Synthesis," Applied and Environmental Microbiology 81(6):1892-1901 (2015).

Finnigan et al., "Characterization of Carboxylic Acid Reductases as Enzymes in the Toolbox for Synthetic Chemistry," ChemCatChem 9:1005-1017 (2017).

Hai et al., "Structure-guided function discovery of an NRPS-like glycine betaine reductase for choline biosynthesis in fungi," PNAS 116(21): 10348-10353 (2019).

SEQUENCE LISTING

```
<160> NUMBER OF SEQ ID NOS: 6

<210> SEQ ID NO 1
<211> LENGTH: 38
<212> TYPE: DNA
<213> ORGANISM: Artificial Sequence
<220> FEATURE:
<223> OTHER INFORMATION: primer sequence

<400> SEQUENCE: 1
attaggtacc aaaaattgtg tcatcgtcag tgcggtac                             38

<210> SEQ ID NO 2
<211> LENGTH: 38
<212> TYPE: DNA
<213> ORGANISM: Artificial Sequence
<220> FEATURE:
<223> OTHER INFORMATION: primer sequence

<400> SEQUENCE: 2
attaaagctt aattcaaccg ttcaatcacc atcgcaat                             38

<210> SEQ ID NO 3
<211> LENGTH: 30
<212> TYPE: DNA
<213> ORGANISM: Artificial Sequence
<220> FEATURE:
<223> OTHER INFORMATION: primer sequence

<400> SEQUENCE: 3
gcatttgcga tttcttttta tcatacgtac                                      30

<210> SEQ ID NO 4
<211> LENGTH: 30
<212> TYPE: DNA
<213> ORGANISM: Artificial Sequence
<220> FEATURE:
<223> OTHER INFORMATION: primer sequence
```

```
<400> SEQUENCE: 4
gtacgtatga taaaaagaaa tcgcaaatgc                                      30

<210> SEQ ID NO 5
<211> LENGTH: 75
<212> TYPE: DNA
<213> ORGANISM: Artificial Sequence
<220> FEATURE:
<223> OTHER INFORMATION: primer sequence

<400> SEQUENCE: 5
attaatccat ggtctagata attaatggat ccaggaggaa acatatgtcg atgataaaaa     60
gctatgccgc aaaag                                                      75

<210> SEQ ID NO 6
<211> LENGTH: 52
<212> TYPE: DNA
<213> ORGANISM: Artificial Sequence
<220> FEATURE:
<223> OTHER INFORMATION: primer sequence

<400> SEQUENCE: 6
attaatccta ggaagcttct cgagtcaaaa atcggctttc aacaccacgc gg             52
```

COMPOSITIONS AND METHODS FOR RECOMBINANT BIOSYNTHESIS OF PROPANE

CROSS-REFERENCE TO RELATED APPLICATIONS

This application is a continuation application of U.S. patent application Ser. No. 15/421,861, filed 1 Feb. 2017, which claims the benefit of then U.S. Provisional Patent Application No. 62/289,517, filed 1 Feb. 2016, each of which is hereby incorporated herein.

SEQUENCE LISTING

The sequence listing contained in the electronic file titled "P32872US2_sequence_listing_ST25.txt," created 31 Jan. 2017, comprising 1 KB, is hereby incorporated herein.

TECHNICAL FIELD

The present invention relates to recombinant (genetically engineered) microorganisms and methods of producing said microorganisms. Also provided are methods for producing biofuels by culturing the recombinant microorganisms.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Propane, a major component of autogas or liquefied petroleum gas (LPG), is an emerging fuel for future energy supply and transportation. Propane is the third most widely used motor fuel and about 20 million tonnes of propane gas are used per year to fuel motor vehicles. It is estimated that propane provides heat and energy for more than fourteen million homes worldwide annually. Propane also has an existing global market for a wide number of other stationary and mobile applications, such as low emission vehicles, gas burners and refrigeration systems. Easy separation from liquid biotechnological processes as a gas and less energy requirements for liquefaction and storage, offers potential advantages to propane over other gaseous fuels.

Natural metabolic pathways for the renewable biosynthesis of propane do not exist. The discovery of an aldehyde deformylating oxygenase (ADO) from cyanobacteria, however, has paved the way for synthetic alkane pathways to be constructed [Schirmer A et al. *Science* 2010, 329:559-562; Akhtar M K et al. *Proc Natl Acad Sci USA* 2013, 110:87-92; Howard T P et al. *Proc Natl Acad Sci USA* 2013, 110:7636-7641]. A microbial platform for propane generation dependent on fatty acid biosynthesis was recently reported [Kallio P et al., *Nature communications* 2014, 5:4731]. Kallio P et al. concluded that the pathway was limited by total flux through fatty acid synthesis (FAS). The most obvious example of this limitation comes from the markedly enhanced rate of propane synthesis observed when fatty acids were supplied to the external media. Herein, the inventors sought to bypass this limitation by generating new synthetic pathways that are not dependent on FAS. The inventors designed a series of modified butyraldehyde pathways based on the CoA-dependent butanol pathways commonly found in *Clostridium* spp. Propane biosynthesis was thereafter achieved by interrupting the route to alcohol by the addition of ADO (FIG. 1).

The butanol pathway in *Clostridium* proceeds either via a keto acid route (Ehrlich pathway) or a CoA-dependent route. Higher yields of branched chain alcohols and aldehyde precursors (e.g. isobutyraldehyde) from the decarboxylation of keto acids make the Ehrlich pathway less attractive because ADO has a strong preference for straight chain aldehyde substrates. By contrast, butanol production by the CoA-dependent route initiates with the condensation of two molecules of acetyl CoA. Reduction in subsequent steps produces the end-product 1-butanol, via a butyraldehyde intermediate. There are several reports of engineered CoA-dependent butanol pathways in *E. coli* and other host organisms [Atsumi S et al. *Nature biotechnology* 2009, 27:1177-1180; Bond-Watts B B et al. *Nat Chem Biol* 2011, 7:222-227; Dellomonaco C et al. *Nature* 2011, 476:355-U131; Lan E I et al. *J C Metab Eng* 2011, 13:353-363; Lan E I. *Proc Natl Acad Sci USA* 2012, 109:6018-6023; Lan E I et al. *Energ Environ Sci* 2013, 6:2672-2681; Pasztor A et al. *Biotechnology and bioengineering* 2014]. Herein, the inventors constructed and evaluated a series of CoA-dependent butyraldehyde pathways that eliminate the dependency on AdhE2, thereby allowing butyraldehyde to be re-routed towards propane instead of butanol.

The use of ADO (from *Prochlorococcus marinus* MIT9313) as a terminal decarbonylase has been used for the production of medium/long chain (C9-C17) as well as short chain-length alkanes (C3, C7). Variant forms of ADO have demonstrated improved activity with the shorter chain aldehydes that are not encountered in native cyanobacteria. These variant forms of ADO are therefore attractive enzyme components for building new synthetic pathways with a greater productivity, as addressed herein.

Propane ($C_3H_8$) is a volatile hydrocarbon with highly favourable physicochemical properties as a fuel, in addition to existing global markets and infrastructure for storage, distribution and utilization in a wide range of applications. Consequently, propane is an attractive target product in research aimed at developing new renewable alternatives to complement currently used petroleum-derived fuels. This study focuses on the construction and evaluation of alternative microbial biosynthetic pathways for the production of renewable propane. The new pathways utilize CoA intermediates that are derived from clostridial-like fermentative butanol pathways and are therefore distinct from the first microbial propane pathways derived from FAS recently engineered in *E. coli*.

SUMMARY

The following embodiments and aspects thereof are described and illustrated in conjunction with systems, compositions and methods which are meant to be exemplary and illustrative, not limiting in scope.

Described herein are the construction and evaluation of novel pathways for butane and propane production in *E. coli* that are independent of the FAS pathway in a recent study [Kallio P et al., *Nature communications* 2014, 5:4731], thereby opening up possibilities for further optimization of short chain-length alkane biosynthesis.

Provided herein are genetically engineered microorganisms for synthesis of propane express or increase expression of a polynucleotide encoding a polypeptide having: (i)

acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(vii) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

Also provided herein are genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(vii) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

Further provided herein are genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In some embodiments, the genetically engineered microorganisms further express or increase expression of a polynucleotide encoding a polypeptide having aldehyde reductase (ahr) activity. In one embodiment, the host organism engineered to express enzymes (i)-(v) is *Escherichia coli*.

Also provided herein are genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In some embodiments, the genetically engineered microorganisms further express or increase expression of a polynucleotide encoding a polypeptide having aldehyde reductase (ahr) activity. In one embodiment, the host organism engineered to express enzymes (i)-(vii) is *Escherichia coli*.

As described herein, genes expressing enzymes for production of propane or butanol may be derived from various microorganisms.

Also provided herein are methods for producing butanol. The methods comprise, consist of or consist essentially of providing the genetically engineered microorganism described herein and culturing the microorganism so as to produce butanol.

Further provided herein are methods for producing propane. The methods comprise, consist of or consist essentially of providing the genetically engineered microorganism described herein and culturing the microorganism so as to produce propane.

The present invention is described in relation to the following clauses:

1. A genetically engineered microorganism capable of producing propane independent of fatty acid synthesis pathways.

2. The genetically engineered microorganism of clause 1, further capable of producing butanol.

3. The genetically engineered microorganism of clause 1, wherein propane is produced independent of aldehyde-alcohol dehydrogenase (AdhE2).

4. The genetically engineered microorganism of clause 3, wherein propane is produced from butyraldehyde as a precursor in the presence of aldehyde deformylating oxygenase (ADO).

5. The genetically engineered microorganism of clause 4, wherein propane production is increased in the presence of aldehyde deformylating oxygenase (ADO) or variants thereof.

6. The genetically engineered microorganism of clause 1, comprising a deletion of aldehyde reductase (ahr) enzyme, alcohol dehydrogenase (ΔyqhD) enzyme or a combination thereof.

7. The genetically engineered microorganism of clause 2, wherein the microorganism has been transformed with a first plasmid vector comprising a first nucleotide sequence encoding a polypeptide having acetyl-CoA acetyltransferase (AtoB) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

8. The genetically engineered microorganism of clause 7, wherein the microorganism has been co-transformed with a second plasmid vector comprising a nucleotide sequence encoding a polypeptide having aldehyde-alcohol dehydrogenase (AdhE2) activity.

9. The genetically engineered microorganism of clause 7, wherein the microorganism has been co-transformed with a second plasmid vector comprising a nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity.

10. The genetically engineered microorganism of clause 2, wherein the microorganism has been transformed with a first plasmid vector comprising a first nucleotide sequence encoding a polypeptide having acetoacetyl-CoA synthase (NphT7) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

11. The genetically engineered microorganism of clause 10, wherein the microorganism has been transformed with a second plasmid vector comprising a nucleotide sequence encoding a polypeptide having aldehyde-alcohol dehydrogenase (AdhE2) activity.

12. The genetically engineered microorganism of clause 10, wherein the microorganism has been co-transformed with a second plasmid vector comprising a nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity.

13. The genetically engineered microorganism of clause 9 or 12, wherein the microorganism has been co-transformed with a third plasmid vector comprising a nucleotide sequence encoding a polypeptide having aldehyde reductase (Ahr) activity.

14. The genetically engineered microorganism of clause 6, wherein the microorganism has been transformed with a first plasmid vector comprising a first nucleotide sequence encoding a polypeptide having acetyl-CoA acetyltransferase (AtoB) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

15. The genetically engineered microorganism of clause 14, wherein the microorganism has been co-transformed with a second plasmid vector comprising a first nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity.

16. The genetically engineered microorganism of clause 14, wherein the microorganism has been transformed with a second plasmid vector comprising a nucleotide sequence encoding a polypeptide having aldehyde-alcohol dehydrogenase (AdhE2) activity.

17. The genetically engineered microorganism of clause 6, wherein the microorganism has been transformed with a first plasmid vector comprising a first nucleotide sequence encoding a polypeptide having acetoacetyl-CoA synthase (NphT7) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

18. The genetically engineered microorganism of clause 17, wherein the microorganism has been co-transformed with a second plasmid vector comprising a first nucleotide sequence encoding a polypeptide having acyl-CoA thioester hydrolase (YciA) activity, a second nucleotide sequence encoding a polypeptide having activity of a maturation factor for phosphopantetheinyl transferase (Sfp) and a third nucleotide sequence encoding a polypeptide having carboxylic acid reductase (Car) activity.

19. The genetically engineered microorganism of clause 17, wherein the microorganism has been co-transformed with a second plasmid vector comprising a nucleotide sequence encoding a polypeptide having aldehyde-alcohol dehydrogenase (AdhE2) activity.

20. The purified genetically engineered microorganism of clause 15, 16, 18 or 19, wherein the microorganism has been co-transformed with a third plasmid vector comprising a nucleotide sequence encoding a polypeptide having aldehyde deformylating oxygenase (ADO) activity.

21. The genetically engineered microorganism of clause 20, wherein the microorganism has been co-transformed with a third plasmid vector comprising a nucleotide sequence encoding a polypeptide having aldehyde deformylating oxygenase activity wherein alanine at position 134 is substituted with phenylalanine ($ADO_{A134F}$).

22. The genetically engineered microorganism of clause 20, wherein the microorganism further comprise a polynucleotide encoding one or more ferredoxins so as to increase supply of electrons.

23. The genetically engineered microorganism of clause 22, the ferredoxin is PetF (ssl0020).

24. The genetically engineered microorganism of clause 23, wherein PetF is derived from *Synechocystis* sp. PCC 6803.

25. The genetically engineered microorganism of clauses 1, 2 or 6, wherein the microorganism is *Escherichia coli*.

26. The genetically engineered microorganism of clauses 7 or 14, wherein the acetyl-CoA acetyltransferase (AtoB) is derived from *Escherichia coli*.

27. The genetically engineered microorganism of clauses 7, 10, 14 or 17, wherein the 3-hydroxybutyrl-CoA dehydrogenase (Hbd) and the 3-hydroxybutyryl-CoA dehydratase (Crt) are derived from *Clostridium acetobutylicum*.

28. The genetically engineered microorganism of clauses 7, 10, 14 or 17, wherein the trans-2-enoyl-CoA reductase (Ter) is derived from *Treponema denticola*.

29. The genetically engineered microorganism of clauses 8, 11, 16 or 19, wherein the aldehyde-alcohol dehydrogenase (AdhE2) is derived from *Clostridium acetobutylicum*.

30. The genetically engineered microorganism of clauses 9, 12, 15 or 18, wherein the acyl-CoA thioester hydrolase (YciA) is derived from *Haemophilus influenza*.

31. The genetically engineered microorganism of clauses 9, 12, 15 or 18, wherein the maturation factor for phosphopantetheinyl transferase (Sfp) is derived from *Bacillus subtilis*.

32. The genetically engineered microorganism of clauses 9, 12, 15 or 18, wherein the carboxylic acid reductase (CAR) is derived from *Mycobacterium marinum*.

33. The genetically engineered microorganism of clauses 10 or 17, wherein acetoacetyl-CoA synthase (NphT7) is derived from *Streptomyces* sp. CL190.

34. The genetically engineered microorganism of clauses 20 or 21, wherein the aldehyde deformylating oxygenase (ADO) is derived from *Prochlorococcus marinus*.

35. The genetically engineered microorganism of any one of clauses 7 to 24, wherein the plasmids are inducible.

36. The genetically engineered microorganism of clause 35, wherein the plasmids comprise promoters inducible by an inducer wherein the inducer is any one or more of IPTG and arabinose.

37. A method for producing butanol comprising:
providing the genetically engineered microorganism of any one of clauses 7 to 13; and culturing the microorganism, so as to produce butanol.

38. The method of clause 37, wherein culturing the microorganisms comprises growing the microorganism in media comprising tryptone, yeast extract, glycerol, dipotassium phosphate, monopotassium phosphate and glucose.

39. A method for producing propane comprising:
providing the genetically engineered microorganism of any one of clauses 14 to 24; and culturing the microorganism, so as to produce propane.

40. The method of clause 39, wherein culturing the microorganisms comprises growing the microorganism in media comprising tryptone, yeast extract, glycerol, dipotassium phosphate, monopotassium phosphate and glucose.

41. The method of clause 37 or 39, wherein the microorganism is cultured in the presence of an inducer.

42. A method for producing a microorganism of clause 1, comprising transforming a microorganism with polynucleotides encoding acetyl-CoA acetyltransferase (AtoB), 3-hydroxybutyrl-CoA dehydrogenase (Hbd), 3-hydroxybutyryl-CoA dehydratase (Crt), trans-2-enoyl-CoA reductase (Ter), acyl-CoA thioester hydrolase (YciA), maturation factor for phosphopantetheinyl transferase (Sfp), and carboxylic acid reductase (CAR).

43. A method for producing a microorganism of clause 1, comprising transforming a microorganism with polynucleotides encoding acetyl-CoA acetyltransferase (AtoB), 3-hydroxybutyrl-CoA dehydrogenase (Hbd), 3-hydroxybutyryl-CoA dehydratase (Crt), trans-2-enoyl-CoA reductase (Ter) and aldehyde-alcohol dehydrogenase (AdhE2).

44. A method for producing a microorganism of clause 1, comprising transforming a microorganism with polynucleotides encoding A method for producing a microorganism of clause 1, comprising transforming a microorganism with polynucleotides encoding acetoacetyl-synthase (NphT7), 3-hydroxybutyrl-CoA dehydrogenase (Hbd), 3-hydroxybutyryl-CoA dehydratase (Crt), trans-2-enoyl-CoA reductase (Ter), acyl-CoA thioester hydrolase (YciA), maturation factor for phosphopantetheinyl transferase (Sfp), and carboxylic acid reductase (CAR).

45. A method for producing a microorganism of clause 1, comprising transforming a microorganism with polynucleotides encoding A method for producing a microorganism of clause 1, comprising transforming a microorganism with polynucleotides encoding acetoacetyl-synthase (NphT7), 3-hydroxybutyrl-CoA dehydrogenase (Hbd), 3-hydroxybutyryl-CoA dehydratase (Crt), trans-2-enoyl-CoA reductase (Ter) and aldehyde-alcohol dehydrogenase (AdhE2).

46. The method of clauses 42, 43, 44 or 45, further comprising transforming a microorganism with polynucleotides encoding any one or more of aldehyde deformylating oxygenase (ADO) or aldehyde deformylating oxygenase activity wherein alanine at position 134 is substituted with phenylalanine (ADO$_{A134F}$) or a combination thereof.

47. The method of clause 46, further comprising deleting nucleotides encoding polypeptides having aldehyde reductase (ahr) activity, alcohol dehydrogenase (ΔyqhD) activity or a combination thereof.

48. A method of producing a microorganism of clause 2, comprising transforming a microorganism with a polynucleotides encoding acetyl-CoA acetyltransferase (AtoB), 3-hydroxybutyrl-CoA dehydrogenase (Hbd), 3-hydroxybutyryl-CoA dehydratase (Crt), trans-2-enoyl-CoA reductase (Ter) and aldehyde-alcohol dehydrogenase (AdhE2).

49. A method of producing a microorganism of clause 2, comprising transforming a microorganism with a polynucleotides encoding acetyl-CoA acetyltransferase (AtoB), 3-hydroxybutyrl-CoA dehydrogenase (Hbd), 3-hydroxybutyryl-CoA dehydratase (Crt), trans-2-enoyl-CoA reductase (Ter), aldehyde-alcohol dehydrogenase, acyl-CoA thioester hydrolase (YciA), maturation factor for phosphopantetheinyl transferase (Sfp), and carboxylic acid reductase (CAR).

50. A method for producing a microorganism of clause 2, comprising transforming a microorganism with polynucleotides encoding A method for producing a microorganism of clause 1, comprising transforming a microorganism with polynucleotides encoding acetoacetyl-synthase (NphT7), 3-hydroxybutyrl-CoA dehydrogenase (Hbd), 3-hydroxybutyryl-CoA dehydratase (Crt), trans-2-enoyl-CoA reductase (Ter) and aldehyde-alcohol dehydrogenase (AdhE2).

51. A method for producing a microorganism of clause 2, comprising transforming a microorganism with polynucleotides encoding acetoacetyl-synthase (NphT7), 3-hydroxybutyrl-CoA dehydrogenase (Hbd), 3-hydroxybutyryl-CoA dehydratase (Crt), trans-2-enoyl-CoA reductase (Ter), aldehyde-alcohol dehydrogenase, acyl-CoA thioester hydrolase (YciA), maturation factor for phosphopantetheinyl transferase (Sfp), and carboxylic acid reductase (CAR).

52. The method of clauses 48, 49, 50 or 51, further comprising transforming the microorganism with a polynucleotide encoding aldehyde reductase (Ahr).

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1A:
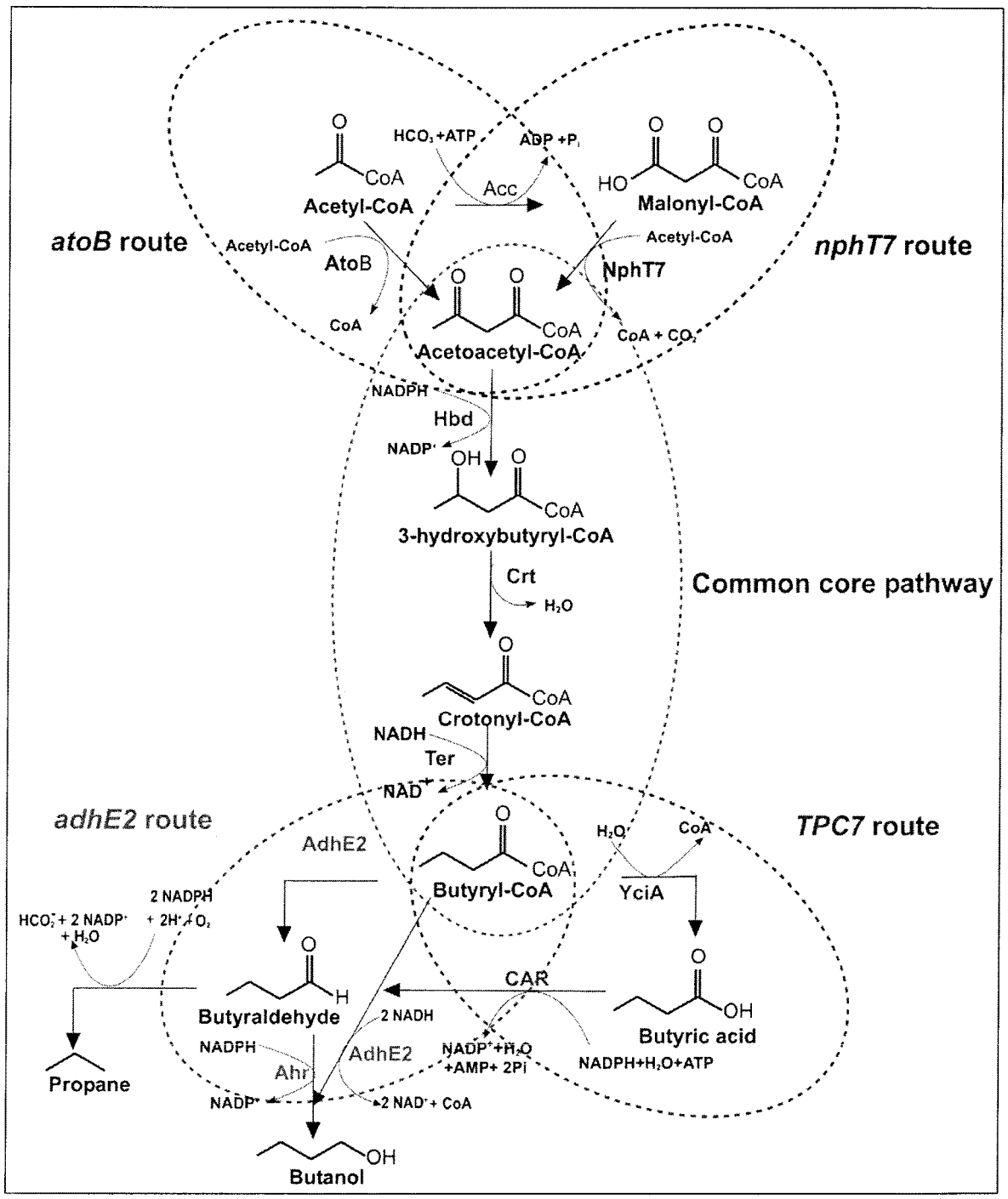
FIGS. 1A and 1B depict in accordance with various embodiments of the invention, the CoA dependent butanol pathways used for the production of propane in *E. coli*. The four CoA dependent butanol producing synthetic routes explored for butanol production in *E. coli* are shown. The four pathways are named as a) atoB-adhE2 route), b) atoB-TPC7 route, c) nphT7-adhE2 route and d) nphT7-TPC7 route. AtoB, acetyl-CoA acetyltransferase; NphT7, acetoacetyl CoA synthase; Hbd, 3-hydroxybutyryl-CoA dehydrogenase; Crt, 3-hydroxybutyryl-CoA dehydratase; Ter, trans-2-enoyl-CoA reductase; AdhE2, aldehyde-alcohol dehydrogenase; Ahr, aldehyde reductase; YciA, acyl-CoA thioester hydrolase; CAR, carboxylic acid reductase; ADO, aldehyde deformylating oxygenase; IPTG, isopropyl β-D-1-thiogalactopyranoside; O.D$_{600}$: optical density at 600 nm; Fdx: ferredoxin.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy $22^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology $3^{rd}$ ed., revised ed., J. Wiley & Sons (New York, N.Y. 2006); Smith, March's Advanced Organic Chemistry Reactions, Mechanisms and Structure $7^{th}$ ed., J. Wiley & Sons (New York, N.Y. 2013); Singleton, Dictionary of DNA and Genome Technology $3^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual $2^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul., 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the terms "recombinant microorganism" or "genetically engineered microorganism" refers to microorganism having expression of or increased expression of one or more target enzymes relative to the parental microorganism or encode one or more enzymes not found in the parental organism. In an embodiment, the microorganism has reduced expression of or absence of expression of one or more genes encoding an enzyme that competes with a metabolite necessary for the production of a desired product or which produces an undesirable product. The recombinant microorganism produces at least one metabolite involved in a biosynthetic pathway for the production of propane. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of propane, butanol or a combination thereof. The target enzyme is encoded by, and expressed from, a polynucleotide derived from a suitable biological source. In some embodiments, the polynucleotide comprises a gene derived from a bacterial, archaeon, plant, or yeast source and recombinantly engineered into the microorganism described herein.

As used herein, the term "metabolically engineered" or "metabolic engineering" refers to rational pathway design and assembly of biosynthetic genes, genes associated with operons, and control elements of such polynucleotides, for the production of a desired metabolite, such as an acetoacetyl-CoA, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate or use of a cofactor or energy source, leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized. In an exemplary embodiment, deletion of competing metabolic pathways as applicable herein include deletion of any one or more of aldehyde reductase enzyme, alcohol dehydrogenase enzyme or a combination thereof, in the host organism.

The term "biosynthetic pathway" or "metabolic pathway" refers to anabolic or catabolic biochemical reactions for converting (transforming) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "substrate" or "suitable substrate" refers to any substance or compound that is converted or meant to be converted into another compound by the action of an enzyme. The term includes a single compound or combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein.

The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

An "enzyme" refers to any substance, typically composed wholly or largely of protein, that catalyzes or promotes, more or less specifically, one or more chemical or biochemical reactions. The term "enzyme" can also refer to a catalytic polynucleotide (e.g., RNA or DNA).

The term "polynucleotide", "nucleic acid" or "recombinant nucleic acid" refers to polynucleotides such as deoxyribonucleic acid (DNA), and, where appropriate, ribonucleic acid (RNA). A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes" that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

A "native" or "wild-type" protein, enzyme, polynucleotide, gene, or cell, means a protein, enzyme, polynucleotide, gene, or cell that occurs in nature.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

The inventors herein report new pathways for propane production based on a fermentative butanol pathway. These are distinct from previously reported pathways that were based on fatty acid synthesis, where propane production is limited by the availability of butyraldehyde precursors and the poor activity of aldehyde deformylating oxygenase (ADO) with butyraldehyde. Herein, the inventors demonstrate that the new pathways are plausible alternatives for the construction of next-generation microbial propane production platforms.

Recombinant Microorganisms

Figure 1B:
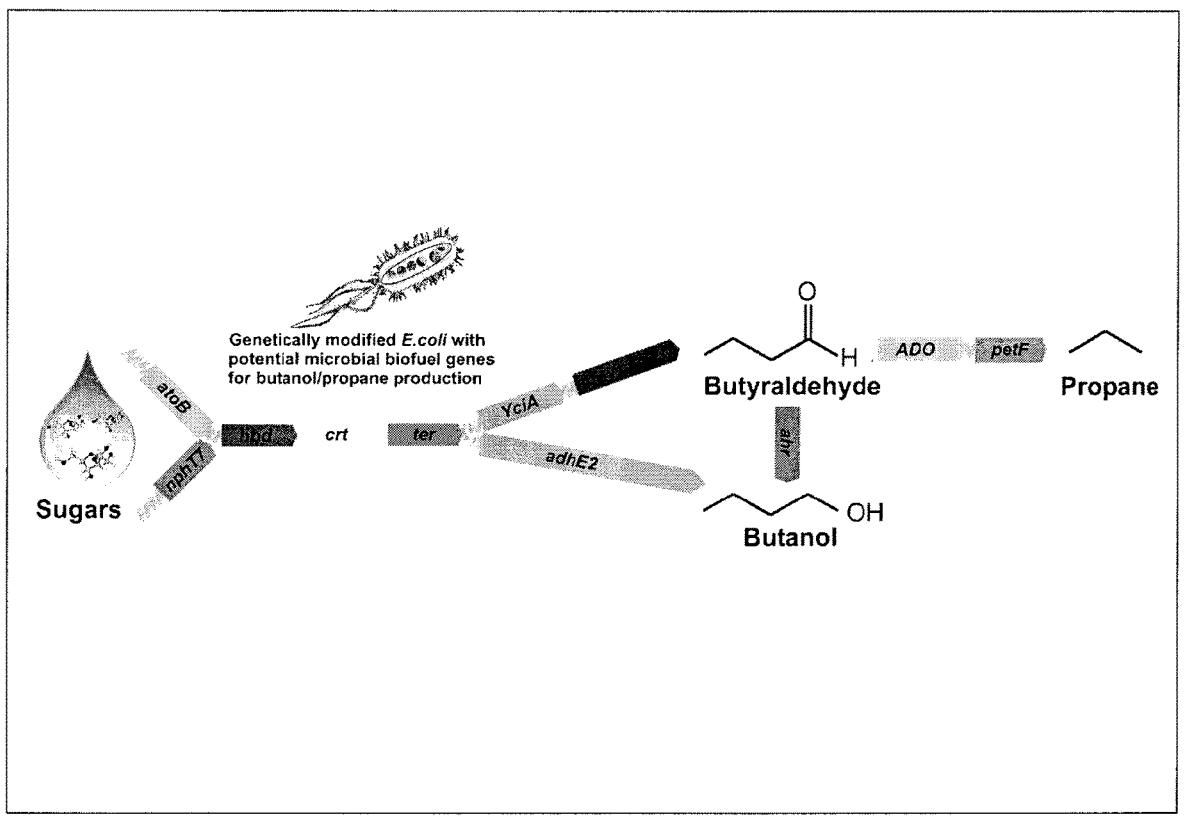

The pathways for propane and butanol production are depicted in FIG. 1. For propane production, the ADO enzyme requires butyraldehyde as a precursor. The inventors constructed two biosynthetic pathways for butyraldehyde synthesis based on the fermentation pathway of 1-butanol, as summarized in FIG. 1. The initial step of the pathway included either acetyl-CoA acetyltransferase (for example, AtoB) or acetoacetyl-CoA synthase (for example, NphT7) to convert the metabolic pathway intermediate, acetyl-CoA to acetoacetyl-CoA. For the second and third steps, 3-hydroxybutyryl-CoA dehydrogenase (for example, Hbd) and 3-hydroxybutyryl-CoA dehydratase (for example, crotonase or Crt) were used to convert acetoacetyl-CoA to crotonyl-CoA. For the fourth step, the oxygen-sensitive flavoenzyme butyryl-CoA dehydrogenase was replaced with NADH-dependent trans-enoyl-CoA reductase (for example, Ter) to reduce crotonyl-CoA to butyryl-CoA. In the final step, butyraldehyde was synthesised by NAD(P)H-dependent reduction of butyl CoA catalysed by aldehyde-alcohol dehydrogenase (AdhE2). The inventors replaced AdhE2 with a thioesterase (for example, YciA) to cleave butyryl-CoA to butyric acid and ATP/NADPH-dependent carboxylic acid reductase (for example, CAR) to convert butyric acid to butyraldehyde, which is a precursor for propane synthesis.

Accordingly, provided herein are genetically engineered microorganisms that can express a plurality of enzymes involved in the pathway for production of propane, butanol or a combination thereof, from a suitable carbon source. Exemplary carbon sources include but are not limited to glucose, glycerol, complex feedstocks (e.g. hydrolysates). In one embodiment, the enzymes are involved in the metabolic pathway for production of propane. The genetically engineered microorganisms described herein produce metabolites in quantities that are higher than the parent microorganism. Examples of metabolites include starting metabolites (such as glucose or glycerol), intermediates (such as acetoacetyl-CoA) and/or end products (such as propane or butanol).

The genetically engineered microorganisms described herein are produced by introduction of genetic material into the parent (host) microorganism so that the microorganism acquires new properties which are not present in the parental microorganism. In exemplary embodiments, new properties include abilities to produce or produce in increased amounts, metabolic enzymes involved in the pathways to produce propane, butanol or a combination thereof. The genetic material may additionally include elements that regulate synthesis of the metabolic enzymes including but not limited to promoter sequences and sequences specific for inducers.

In one embodiment, genetically engineered microorganisms for synthesis of propane express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(vii) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

In another embodiment, genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(vii) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

In a further embodiment, genetically engineered microorganisms for synthesis of propane express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(v) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

In a further embodiment, genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In an embodiment, the microorganisms further express or increase expression of a polynucleotide encoding a polypeptide having aldehyde deformylating oxygenase activity (for example, ado). In one embodiment, the host/parent organism engineered to express enzymes (i)-(v) and aldehyde deformylating oxygenase (Ado) is *Escherichia coli*. In an embodiment, propane synthesis set forth herein is independent of aldehyde-alcohol dehydrogenase and fatty acid synthesis. In some embodiments, propane is produced by utilizing butyraldehyde as a precursor.

As described herein, in some embodiments, the genetically engineered microorganisms for propane production express wild type aldehyde deformylating oxygenase (for example, ado). In some embodiments, the genetically engineered microorganisms for propane production express mutant form of aldehyde deformylating oxygenase. In an embodiment, the mutation in aldehyde deformylating oxygenase results in increased production of propane. In an exemplary embodiment, the genetically engineered microorganisms for propane production comprises a polynucleotide encoding the polypeptide having aldehyde deformylating oxygenase activity comprises, consists of or consists essentially of an amino acid substitution at position 134 from alanine to phenylalanine.

In some embodiments, the genetically engineered microorganisms for propane production described herein further comprise iron-sulfur proteins (for example, ferredoxin PetF) having electron transfer activity so as to increase supply of electrons to ADO, thereby increasing propane production.

In some embodiments, the parent of the genetically engineered microorganism for propane production comprises deletion of competing pathways so as to increase propane production. In an exemplary embodiment, deletion of any one or more of aldehyde reductase enzyme (for example, deletion of ahr (Δahr)), alcohol dehydrogenase enzyme (for example, deletion of yqhD (ΔyqhD)) or a combination thereof, increases propane production.

In an embodiment, genetically engineered microorganisms for synthesis of propane express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In an embodiment, the microorganisms further express polynucleotides encoding ferredoxins (for example, PetF). In one embodiment, the host/parent organism engineered to express enzymes (i)-(vii), aldehyde deformylating oxygenase (Ado) and PetF is *Escherichia coli*. In an embodiment, the host organism includes deletion of any one or more of aldehyde reductase enzyme (for example, deletion of ahr (Δahr), alcohol dehydrogenase enzyme (for example, deletion of yqhD (ΔyqhD) or a combination thereof. In an embodiment, propane synthesis set forth herein is independent of aldehyde-alcohol dehydrogenase and fatty acid synthesis. In some embodiments, propane is produced by utilizing butyraldehyde as a precursor.

In another embodiment, genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) activity of a maturation factor for phosphopantetheinyl transferase (for example, sfp); and (vii) carboxylic acid reductase activity (for example, car). In an embodiment, the microorganisms further express or increase expression of a polynucleotide encoding a polypeptide having aldehyde deformylating oxygenase activity (for example, ado). In an embodiment, the microorganisms further express polynucleotides encoding ferredoxins (for example, PetF). In one embodiment, the host/parent organism engineered to express enzymes (i)-(vii), aldehyde deformylating oxygenase (Ado) and PetF is *Escherichia coli*. In an embodiment, the host organism includes deletion of any one or more of aldehyde reductase enzyme (for example, deletion of ahr (Δahr)), alcohol dehydrogenase enzyme (for example, deletion of yqhD (ΔyqhD)) or a combination thereof. In an embodiment, propane synthesis set forth herein is independent of aldehyde-alcohol dehydrogenase and fatty acid synthesis. In some embodiments, propane is produced by utilizing butyraldehyde as a precursor.

In an embodiment, genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In some embodiments, the genetically engineered microorganisms further express or increase expression of a polynucleotide encoding a polypeptide having aldehyde reductase (ahr) activity. In one embodiment, the host organism engineered to express enzymes (i)-(v) is *Escherichia coli*.

In another embodiment, genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In some embodiments, the genetically engineered microorganisms further express or increase expression of a polynucleotide encoding a polypeptide having aldehyde reductase (ahr) activity. In one embodiment, the host organism engineered to express enzymes (i)-(vii) is *Escherichia coli*.

In a further embodiment, genetically engineered microorganisms for synthesis of butanol express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In some embodiments, the genetically engineered microorganisms further express or increase expression of a polynucleotide encoding a polypeptide having aldehyde reductase (ahr) activity. In one embodiment, the host organism engineered to express enzymes (i)-(v) is *Escherichia coli*.

In another embodiment, genetically engineered microorganisms for synthesis of butanol express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) activity of a maturation factor for phosphopantetheinyl transferase (for example, sfp) and (vii) carboxylic acid reductase activity (for example, car). In some embodiments, the genetically engineered microorganisms further express or increase expression of a polynucleotide encoding a polypeptide having aldehyde reductase (ahr) activity. In one embodiment, the host organism engineered to express enzymes (i)-(vii) is *Escherichia coli*.

As described herein, each enzyme produced by the genetically engineered microorganisms described herein produce metabolites. In one embodiment, the genetically engineered microorganisms described herein express a thiolase to produce the metabolite acetoacetyl-CoA from two molecules of acetyl-CoA. In one embodiment, the thiolase is encoded by an atoB gene or a homolog thereof and encodes the polypeptide having acetyl-CoA acetyltransferase activity. The atoB gene may be derived from any biological source including but not limited to *Escherichia coli, Clostridium acetobutylicum Klebsiella pneumonia, Pseudomonas fluorescens* F113, *Helicobacter acinonychis* st. Sheeba and *Desulfobacterium autotrophicum*.

In another embodiment, the genetically engineered microorganisms described herein express an acetoacetyl-CoA synthase to produce the metabolite acetoacetyl-CoA from acetyl-CoA and malonyl-CoA. In an exemplary embodiment, the acetoacetyl-CoA synthase is encoded by an nphT7 gene or a homolog thereof and can be derived from any biological source including but not limited to *Streptomyces* sp. CL190, *Paenibacillus* sp. P1XP2, *Legionella pneumophila* and *Microbacterium ketosireducens*.

In a further embodiment, genetically engineered microorganisms described herein express oxidoreductases such as 3-hydroxybutyryl-CoA dehydrogenase to produce the metabolite 3-hydroxybutyryl-CoA from a substrate that includes acetoacetyl-CoA. In an exemplary embodiment, the 3-hydroxybutyryl-CoA dehydrogenase is encoded by an hbd gene or homolog thereof and can be derived from any biological source including but not limited to *Clostridium acetobutylicum, Clostridium difficile, Butyrivibrio fibrisolvens, Treponema phagedenis, Acidaminococcus fermentans, Clostridium kluyveri*, and *Thermoanaerobacterium thermosaccharolyticum*. In one embodiment, the hbd gene is derived from *Clostridium acetobutylicum*.

In an additional embodiment, genetically engineered microorganisms described herein express lyases (for example, hydro-lyases) such as 3-hydroxybutyryl-CoA dehydratase to produce the metabolite crotonoyl-CoA from a substrate that includes 3-hydroxybutyryl-CoA. In an exemplary embodiment, the 3-hydroxybutyryl-CoA dehydratase is encoded by a crt gene or a homolog thereof and can be derived from any biological source including but not limited to *Clostridium acetobutylicum, Butyrivibrio fibrisolvens, Thermoanaerobacterium thermosaccharolyticum, Methylobacterium extorquens, Dictyostelium discoideum, Clostridium pasteurianum, Mycobacterium smegmatis* and *Clostridium difficile*. In one embodiment, the crt gene is derived from *Clostridium acetobutylicum*.

In a further embodiment, genetically engineered microorganisms described herein express additional oxidoreductases such as trans-2-enoyl-CoA reductase (TER) to produce the metabolite butyryl-CoA from a substrate that includes crotonoyl-CoA. In an exemplary embodiment, the trans-2-enoyl-CoA reductase is encoded by the ter gene or a homolog thereof and can be derived from any biological source including but not limited to *Treponema denticola, Clostridium acetobutylicum, Euglena gracilis, Paenibacillus* sp. FSL R5-808 and *Fibrobacter succinogenes*. In one embodiment, the ter gene is derived from *Treponema denticola*.

In another embodiment, genetically engineered microorganisms described herein express hydrolases (for example, those acting on thioester bonds) such as acyl-CoA thioester hydrolase to produce the metabolite butyric acid from a substrate that includes butyryl-CoA. In an exemplary embodiment, the acyl-CoA thioester hydrolase is encoded by the yciA or Acot gene or a homolog thereof and can be derived from any biological source including but not limited to *Campylobacter jejuni, Haemophilus influenza, Escherichia coli, Rattus norvegicus, Deinococcus peraridilitoris, Chlamydia pneumonia, Shigella flexneri, Zymomonas mobilis* subsp. *Mobilis, Enterobacter cloacae* and *Acinetobacter* sp. ADP1. In one embodiment the yciA gene is derived from *Haemophilus influenza*.

In a further embodiment, genetically engineered microorganisms described herein express additional oxidoreductases (for example, those acting on aldehyde groups) such as carboxylic acid reductase to produce the metabolite butyraldehyde from a substrate that includes butyric acid. In an exemplary embodiment, the carboxylic acid reductase is encoded by the car gene or a homolog thereof and can be derived from any biological source including but not limited to *Mycobacterium marinum, Streptomyces* sp. W007, *Tolypocladium ophioglossoides* CBS 100239, *Mycobacterium obuense* and *Nocardia iowensis*. In one embodiment the yciA gene is derived from *Mycobacterium marinum*.

In another embodiment, genetically engineered microorganisms described herein express alcohol dehydrogenases such as aldehyde-alcohol dehydrogenase to produce the metabolite butanol from a substrate that includes butyryl-CoA. In an exemplary embodiment, the alcohol dehydrogenase can be encoded by bdhA/bdhB gene or homolog thereof, an aad gene, or homolog thereof, or an adhE2 gene or homolog thereof. The aad gene or adhE2 can be derived from *Clostridium acetobutylicum*.

In an embodiment, genetically engineered microorganisms described herein express aldehyde deformylating oxygenase (ADO) to produce the metabolite propane from the substrate butyraldehyde. In an exemplary embodiment, aldehyde deformylating oxygenase is derived from *Prochlorococcus marinus*.

In an embodiment, genetically engineered microorganisms described herein express iron-sulfur proteins so as to increase electron supply and thereby increase ADO-dependent propane production. In an exemplary embodiment, the iron-sulfur protein is ferredoxin PetF or a homolog thereof and may be derived from any biological source including but not limited to *Synechocystis* sp. PCC 6803, *Thermosynechococcus elongatus* st. BP-1, *Acaryochloris marina* st. MBIC 11017, *Roseobacter litoralis, Planktothrix agardhii, Octadecabacter arcticus* 238 and *Nostoc* sp. strain ATCC 29151.

The instant disclosure identifies genes useful in the methods, compositions and organisms of the disclosure. However it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme activity using methods known in the art.

In addition, homologs of enzymes useful for generating metabolites (such as propane and/or butanol) are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

In some embodiments, the amount of propane produced by the genetically engineered microorganisms is any one or more of at least about 100 µg/L, at least about 200 µg/L, at least about 300 µg/L, at least about 400 µg/L, at least about 500 µg/L, at least about 600 µg/L, at least about 700 µg/L, at least about 800 µg/L, at least about 900 µg/L, at least about 1 mg/L, at least about 2 mg/L, at least about 3 mg/L, at least about 4 mg/L, at least about 5 mg/L, at least about 6 mg/L, at least about 7 mg/L, at least about 8 mg/L, at least about 9 mg/L, at least about 10 mg/L or combinations thereof, in, for example, 72 hours. In some embodiments, propane production by the genetically engineered microorganisms is higher in the presence of any one or more of deletion of competing pathways, $ADO_{A134F}$, ferredoxin-based electron supply system or a combination thereof.

In some embodiments, the amount of butanol produced by the genetically engineered microorganisms is any one or more of at least about 100 mg/L, at least about 200 mg/L, at least about 300 mg/L, at least about 400 mg/L, at least about 500 mg/L, at least about 600 mg/L, at least about 700 mg/L, at least about 800 mg/L, at least about 900 mg/L, at least about 1000 mg/L or combinations thereof, in, for example, 72 hours.

Methods

Provided herein are methods for producing butanol. The methods comprise, consist of or consist essentially of providing the genetically engineered microorganism described herein and culturing the microorganism so as to produce butanol.

In one embodiment of the method for producing butanol, the genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In some embodiments, the genetically engineered microorganisms for synthesis of butanol further express or increase expression of a polynucleotide encoding a polypeptide having aldehyde reductase (Ahr) activity. In one embodiment, the host organism engineered to express enzymes (i)-(vii) is *Escherichia coli*.

In another embodiment of the method for producing butanol, genetically engineered microorganisms for synthesis of butanol express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In some embodiments, the genetically engineered microorganisms for synthesis of butanol further express or increase expression of a polynucleotide encoding a polypeptide having aldehyde reductase (Ahr) activity. In one embodiment, the host organism engineered to express enzymes (i)-(v) is *Escherichia coli*.

In a further embodiment of the method for producing butanol, genetically engineered microorganisms for synthesis of butanol express or increase expression of a polynucleotide encoding a polypeptide having (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and (v) aldehyde-alcohol dehydrogenase activity (for example, adhE2). In some embodiments, the genetically engineered microorganisms for synthesis of butanol express or increase expression of a polynucleotide encoding a polypeptide having aldehyde reductase (Ahr) activity. In one embodiment, the host organism engineered to express enzymes (i)-(v) is *Escherichia coli*.

In a further embodiment of the method for producing butanol, genetically engineered microorganisms for synthesis of butanol express or increase expression of a polynucleotide encoding a polypeptide having (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); v) acyl-CoA thioester hydrolase activity (for example, yciA); (vi) the activity of a maturation factor for phosphopantetheinyl transferase (for example, sfp); and (vii) carboxylic acid reductase activity (for example, car). In some embodiments, the genetically engineered microorganisms for synthesis of butanol further express or increase expression of a polynucleotide encoding a polypeptide having aldehyde reductase (Ahr) activity. In one embodiment, the host organism engineered to express enzymes (i)-(vii) is *Escherichia coli*.

Provided herein are methods for producing propane. The methods comprise, consist of or consist essentially of providing the genetically engineered microorganism described herein and culturing the microorganism so as to produce propane. In one embodiment of the method for producing propane, the genetically engineered microorganisms for synthesis of propane express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) the activity of a maturation factor for phosphopantetheinyl transferase (for example, sfp); and (vii) carboxylic acid reductase activity (for example, car). In some embodiments, the genetically engineered microorganisms for synthesis of propane further express or increase expression of aldehyde deformylating oxygenase activity (for example, ado). In some embodiments, the genetically engineered microorganism further encodes a ferredoxin so as to increase electron supply and thus increase propane production. In some embodiments, the parent of the genetically engineered microorganism comprises deletion of one or more of aldehyde reductase enzyme (for example, deletion of ahr), alcohol dehydrogenase enzyme (for example, deletion of yqhD) or a combination thereof, so as to increase the amount of propane synthesized. In some embodiments, aldehyde deformylating oxygenase (for example, ado) is wild type. In some embodiments, aldehyde deformylating oxygenase is a mutant, wherein the mutation results in increased production of propane. In an exemplary embodiment, the polynucleotide encoding the polypeptide having aldehyde deformylating oxygenase activity comprises, consists of or consists essentially of an amino acid substitution at position 134 from alanine to phenylalanine. In an embodiment, propane synthesis set forth herein is independent of aldehyde-alcohol dehydrogenase and fatty acid synthesis. In some embodiments, propane is produced by utilizing butyraldehyde as a precursor. In one embodiment, the host organism engineered to express enzymes (i)-(viii) is *Escherichia coli*. In another embodiment of the method for producing propane, genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); (v) acyl-CoA thioester hydrolase activity (for example, yciA); (vi) activity of a maturation factor for phosphopantetheinyl transferase (for example, sfp); and (vii) carboxylic acid reductase activity (for example, car). In some embodiments, the genetically engineered microorganisms for synthesis of propane further express or increase expression of aldehyde deformylating oxygenase activity (for example, ado). In some embodiments, the genetically engineered microorganism further encodes a ferredoxin so as to increase electron supply and thus increase propane production. In some embodiments, the parent of the genetically engineered microorganism comprises deletion of one or more of aldehyde reductase enzyme (for example, deletion of ahr), alcohol dehydrogenase enzyme (for example, deletion of yqhD) or a combination thereof, so as to increase the amount of propane synthesized. In some embodiments, aldehyde deformylating oxygenase (for example, ado) is wild type. In some embodiments, aldehyde deformylating oxygenase is a mutant, wherein the mutation results in increased production of propane. In an exemplary embodiment, the polynucleotide encoding the polypeptide having aldehyde deformylating oxygenase activity comprises, consists of or consists essentially of an amino acid substitution at position 134 from alanine to phenylalanine. In an embodiment, propane synthesis set forth herein is independent of aldehyde-alcohol dehydrogenase and fatty acid synthesis. In some embodiments, propane is produced by utilizing butyraldehyde as a precursor. In one embodiment, the host organism engineered to express enzymes (i)-(viii) is *Escherichia coli*.

In another embodiment of the method for producing propane, genetically engineered microorganisms for synthesis of propane express or increase expression of a polynucleotide encoding a polypeptide having: (i) acetyl-CoA acetyltransferase activity (for example, atoB); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and v) aldehyde-alcohol dehydrogenase activity (for example, adhE2). In some embodiments, the genetically engineered microorganisms for synthesis of propane further express or increase expression of aldehyde deformylating oxygenase activity (for example, ado). In some embodiments, the genetically engineered microorganism further encodes a ferredoxin so as to increase electron supply and thus increase propane production. In some embodiments, the parent of the genetically engineered microorganism comprises deletion of one or more of aldehyde reductase enzyme (for example, deletion of ahr), alcohol dehydrogenase enzyme (for example, deletion of yqhD) or a combination thereof, so as to increase the amount of propane synthesized. In some embodiments, aldehyde deformylating oxygenase (for example, ado) is wild type. In some embodiments, aldehyde deformylating oxygenase is a mutant, wherein the mutation results in increased production of propane. In an exemplary embodiment, the polynucleotide encoding the polypeptide having aldehyde deformylating oxygenase activity comprises, consists of or consists essentially of an amino acid substitution at position 134 from alanine to phenylalanine. In an embodiment, propane synthesis set forth herein is independent of aldehyde-alcohol dehydrogenase and fatty acid synthesis. In some embodiments, propane is produced by utilizing butyraldehyde as a precursor. In one embodiment, the host organism engineered to express enzymes (i)-(viii) is *Escherichia coli*.

In another embodiment of the method for producing propane, genetically engineered microorganisms for synthesis of propane express or increase expression of a polynucleotide encoding a polypeptide having: (i) acetoacetyl-CoA synthase activity (for example, nphT7); (ii) 3-hydroxybutyrl-CoA dehydrogenase activity (for example, hbd); (iii) 3-hydroxybutyryl-CoA dehydratase activity (for example, crt); (iv) trans-2-enoyl-CoA reductase activity (for example, ter); and v) aldehyde-alcohol dehydrogenase activity (for example, adhE2). In some embodiments, the genetically engineered microorganisms for synthesis of propane further express or increase expression of aldehyde deformylating oxygenase activity (for example, ado). In some embodiments, the genetically engineered microorganism further encodes a ferredoxin so as to increase electron supply and thus increase propane production. In some embodiments, the parent of the genetically engineered microorganism comprises deletion of one or more of aldehyde reductase enzyme (for example, deletion of ahr), alcohol dehydrogenase enzyme (for example, deletion of yqhD) or a combination thereof, so as to increase the amount of propane synthesized. In some embodiments, aldehyde deformylating oxygenase (for example, ado) is wild type. In some embodiments, aldehyde deformylating oxygenase is a mutant, wherein the mutation results in increased production of propane. In an exemplary embodiment, the polynucleotide encoding the polypeptide having aldehyde deformylating oxygenase activity comprises, consists of or consists essentially of an amino acid substitution at position 134 from alanine to phenylalanine. In an embodiment, propane synthesis set forth herein is independent of aldehyde-alcohol dehydrogenase and fatty acid synthesis. In some embodiments, propane is produced by utilizing butyraldehyde as a precursor. In one embodiment, the host organism engineered to express enzymes (i)-(viii) is *Escherichia coli*.

Also provided herein are methods for producing a microorganism capable of producing propane. In an embodiment, the methods comprise, consist of or consist essentially of transforming a microorganism with polynucleotides encoding acetyl-CoA acetyltransferase (AtoB), 3-hydroxybutyrl-CoA dehydrogenase (Hbd), 3-hydroxybutyryl-CoA dehydratase (Crt), trans-2-enoyl-CoA reductase (Ter), acyl-CoA thioester hydrolase (YciA), maturation factor for phosphopantetheinyl transferase (Sfp) and carboxylic acid reductase (CAR) activity. In one embodiment, the method further includes transforming a microorganism with polynucleotides encoding a ferredoxin so as to increase electron supply and thus increase propane production. In one embodiment, the method further includes transforming a microorganism with polynucleotides encoding any one or more of aldehyde deformylating oxygenase (ADO) or aldehyde deformylating oxygenase activity wherein alanine at position 134 is substituted with phenylalanine ($ADO_{A134F}$) or a combination thereof. In an additional embodiment, the method includes deleting nucleotides encoding competing pathways (for example, deleting nucleotides encoding polypeptides having aldehyde reductase activity, alcohol dehydrogenase activity or a combination thereof).

In another embodiment, the methods for producing microorganisms capable of producing propane comprise, consist of or consist essentially of transforming a microorganism with polynucleotides encoding (i) acetoacetyl-CoA synthase (for example, nphT7); (ii) 3-hydroxybutyrl-CoA dehydrogenase (for example, hbd); (iii) 3-hydroxybutyryl-CoA dehydratase (for example, crt); (iv) trans-2-enoyl-CoA reductase (for example, ter); (v) acyl-CoA thioester hydrolase (for example, yciA); (vi) activity of a maturation factor for phosphopantetheinyl transferase (for example, sfp); and (vii) carboxylic acid reductase (for example, car). In one embodiment, the method further includes transforming a microorganism with polynucleotides encoding a ferredoxin so as to increase electron supply and thus increase propane production. In one embodiment, the method further includes transforming a microorganism with polynucleotides encoding any one or more of aldehyde deformylating oxygenase (ADO) or aldehyde deformylating oxygenase activity wherein alanine at position 134 is substituted with phenylalanine ($ADO_{A134F}$) or a combination thereof. In an additional embodiment, the method includes deleting nucleotides encoding competing pathways (for example, deleting nucleotides encoding polypeptides having aldehyde reductase activity, alcohol dehydrogenase activity or a combination thereof).

In a further embodiment, the methods for producing microorganisms capable of producing propane comprise, consist of or consist essentially of transforming a microorganism with polynucleotides encoding (i) acetyl-CoA acetyltransferase (for example, atoB); (ii) 3-hydroxybutyrl-CoA dehydrogenase (for example, hbd); (iii) 3-hydroxybutyryl-CoA dehydratase (for example, crt); (iv) trans-2-enoyl-CoA reductase (for example, ter); and v) aldehyde-alcohol dehydrogenase activity (for example, adhE2). In one embodiment, the method further includes transforming a microorganism with polynucleotides encoding a ferredoxin so as to increase electron supply and thus increase propane production. In one embodiment, the method further includes transforming a microorganism with polynucleotides encoding any one or more of aldehyde deformylating oxygenase (ADO) or aldehyde deformylating oxygenase activity wherein alanine at position 134 is substituted with phenylalanine ($ADO_{A134F}$) or a combination thereof. In an additional embodiment, the method includes deleting nucleotides encoding competing pathways (for example, deleting nucleotides encoding polypeptides having aldehyde reductase activity, alcohol dehydrogenase activity or a combination thereof). In an embodiment, the methods for producing microorganisms capable of producing propane comprise, consist of or consist essentially of transforming a microorganism with polynucleotides encoding (i) acetoacetyl-CoA synthase (for example, nphT7); (ii) 3-hydroxybutyrl-CoA dehydrogenase (for example, hbd); (iii) 3-hydroxybutyryl-CoA dehydratase (for example, crt); (iv) trans-2-enoyl-CoA reductase (for example, ter); and v) aldehyde-alcohol dehydrogenase (for example, adhE2). In one embodiment, the method further includes transforming a microorganism with polynucleotides encoding a ferredoxin so as to increase electron supply and thus increase propane production. In one embodiment, the method further includes transforming a microorganism with polynucleotides encoding any one or more of aldehyde deformylating oxygenase (ADO) or aldehyde deformylating oxygenase activity wherein alanine at position 134 is substituted with phenylalanine ($ADO_{A134F}$) or a combination thereof. In an additional embodiment, the method includes deleting nucleotides encoding competing pathways (for example, deleting nucleotides encoding polypeptides having aldehyde reductase activity, alcohol dehydrogenase activity or a combination thereof).

Also provided herein are methods for producing a microorganism capable of producing butanol. In one embodiment, the methods comprise, consist of or consist essentially of transforming a microorganism with polynucleotides encoding (i) acetyl-CoA acetyltransferase (AtoB), (ii) 3-hydroxybutyrl-CoA dehydrogenase (Hbd), (iii) 3-hydroxybutyryl-CoA dehydratase (Crt), (iv) trans-2-enoyl-CoA reductase (Ter), and (v) aldehyde-alcohol dehydrogenase (AdhE2). In some embodiments, the methods include transforming the microorganism with polynucleotides encoding aldehyde reductase (Ahr).

In another embodiment, the methods for producing a microorganism capable of producing butanol comprise, consist of or consist essentially of transforming a microorganism with polynucleotides encoding (i) acetyl-CoA acetyltransferase (AtoB), (ii) 3-hydroxybutyryl-CoA dehydrogenase (Hbd), (iii) 3-hydroxybutyryl-CoA dehydratase (Crt), (iv) trans-2-enoyl-CoA reductase (Ter), (v) acyl-CoA thioester hydrolase (for example, yciA); (vi) activity of a maturation factor for phosphopantetheinyl transferase (for example, sfp); and (vii) carboxylic acid reductase (for example, car). In some embodiments, the methods include transforming the microorganism with polynucleotides encoding aldehyde reductase (Ahr).

In a further embodiment, the methods for producing a microorganism capable of producing butanol comprise, consist of or consist essentially of transforming a microorganism with polynucleotides encoding (i) acetoacetyl-CoA synthase (for example, nphT7); (ii) 3-hydroxybutyrl-CoA dehydrogenase (for example, hbd); (iii) 3-hydroxybutyryl-CoA dehydratase (for example, crt); (iv) trans-2-enoyl-CoA reductase (for example, ter); (v) acyl-CoA thioester hydrolase (for example, yciA); (vi) activity of a maturation factor for phosphopantetheinyl transferase (for example, sfp); and (vii) carboxylic acid reductase (for example, car). In some embodiments, the methods include transforming the microorganism with polynucleotides encoding aldehyde reductase (Ahr).

In another embodiment, the methods for producing a microorganism capable of producing butanol comprise, consist of or consist essentially of transforming a microorganism with polynucleotides encoding (i) acetoacetyl-CoA synthase (for example, nphT7); (ii) 3-hydroxybutyrl-CoA dehydrogenase (for example, hbd); (iii) 3-hydroxybutyryl-CoA dehydratase (for example, crt); (iv) trans-2-enoyl-CoA reductase (for example, ter), and (v) aldehyde-alcohol dehydrogenase (AdhE2). In some embodiments, the methods include transforming the microorganism with polynucleotides encoding aldehyde reductase (Ahr).

In some embodiments, the vectors in the genetically engineered microorganism encoding enzymes comprise an inducible promoter so as to increase synthesis of the enzymes. In exemplary embodiments, the promoters are isopropyl β-D-1-thiogalactopyranoside (IPTG) or arabinose inducible.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Herein, the inventors report the assembly and evaluation of four different synthetic pathways for the production of propane and butanol, designated a) atoB-adhE2 route), b) atoB-TPC7 route, c) nphT7-adhE2 route and d) nphT7-TPC7 route. The highest butanol titres were achieved with the atoB-adhE2 (473±3 mg/L) and atoB-TPC7-Ahr (163±2 mg/L) routes. When aldehyde deformylating oxygenase (ADO) was co-expressed with these pathways the engineered hosts also produced propane. The atoB-TPC7-ADO pathway was the most effective in producing propane (220±3 µg/L). By (i) deleting competing pathways, (ii) including a previously designed $ADO_{A134F}$ variant with an enhanced specificity towards short-chain substrates, and (iii) including and ferredoxin-based electron supply system, the propane titre was increased (3.40±0.19 mg/L).

This study expands the metabolic toolbox for renewable propane and butanol production and provides new insight and understanding for the development of next-generation biofuel platforms. In developing an alternative CoA dependent fermentative butanol pathway, which includes an engineered ADO variant ($ADO_{A134F}$), the study addresses known limitations, including the low bio-availability of butyraldehyde precursors and poor activity of ADO with butyraldehyde.

Example 1

Experimental Methods

All chemicals, solvents and standards were purchased from Sigma-Aldrich and Fisher Scientific, and were of analytical grade. Media components were obtained from Formedium (Norfolk, UK). Gene sequencing and oligonucleotide synthesis were performed by Eurofins MWG (Ebersberg, Germany). D-Glucose (GOPOD Format) assay kit was from Megazyme.

Strains and Plasmids.

Figure 7:
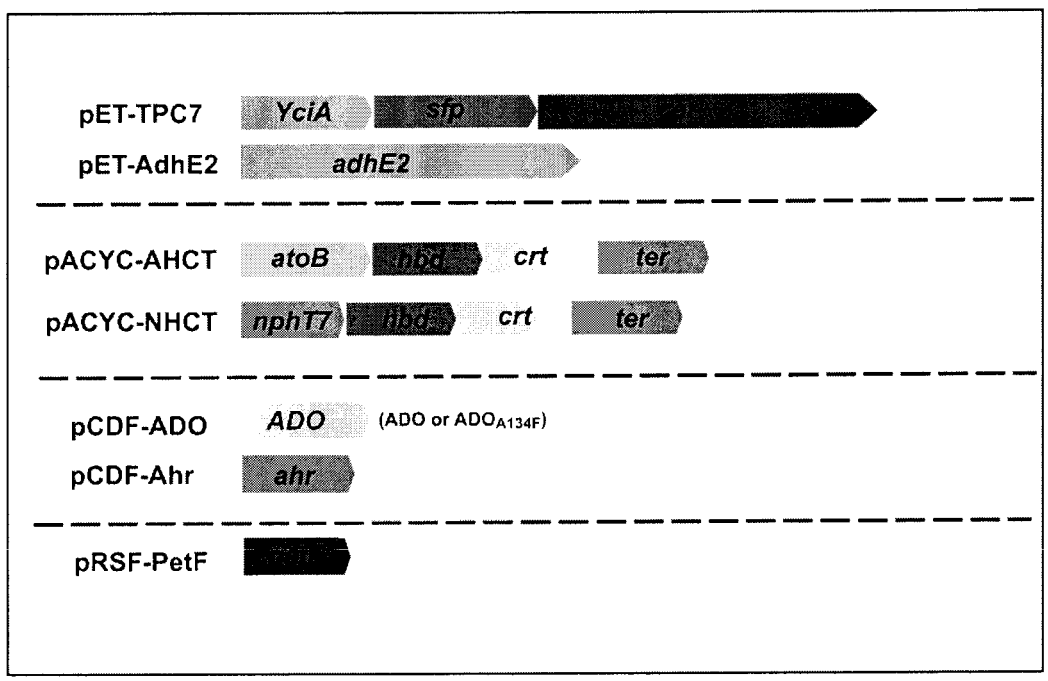
FIG. 7 depicts in accordance with various embodiments of the invention, the plasmid design used to construct engineered propane producing pathways in *E. coli*. The structure of all plasmids used in this study for *E. coli* pathway engineering is shown.
Figure 8:
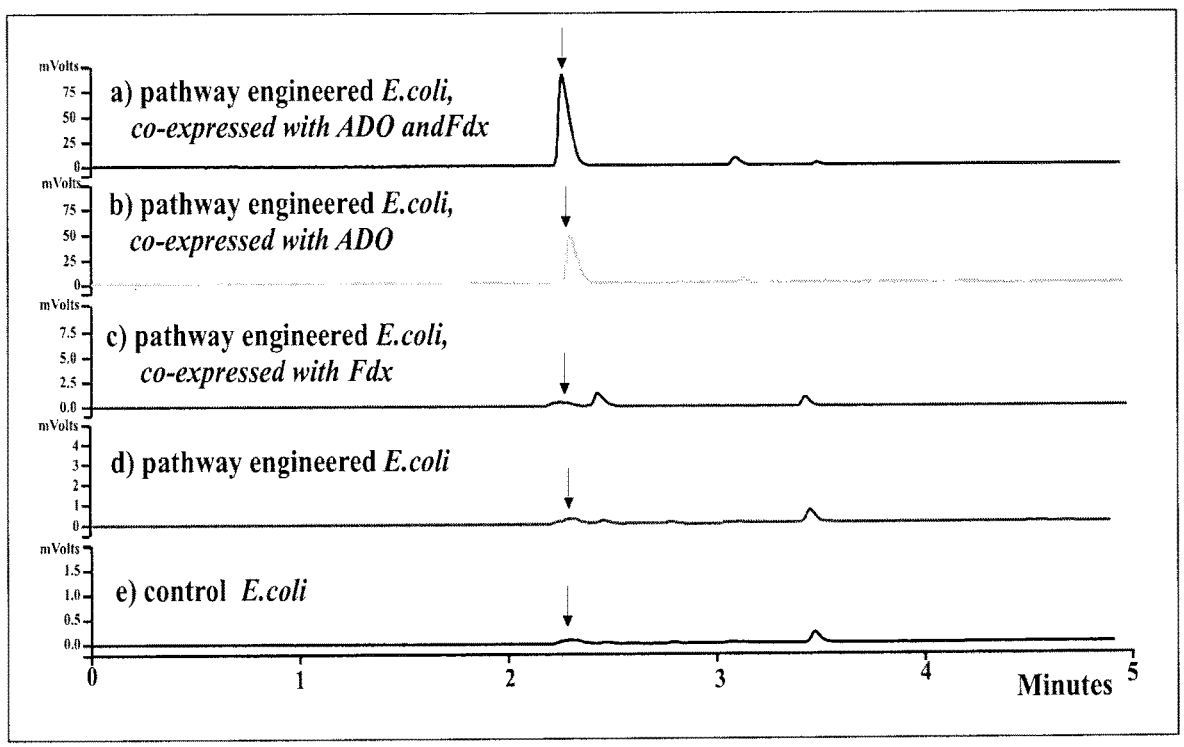
FIG. 8 depicts in accordance with various embodiments of the invention, GC traces and the corresponding propane peak integrated for pathway analysis. GC traces showing the integrated propane peak for the AtoB-TPC7 route containing *E. coli* BL21 strains coexpressed with ADO and ferredoxin (trace a), AtoB-TPC7 route containing *E. coli* BL21 strains coexpressed with ADO (trace b), AtoB-TPC7 route engineered in *E. coli* BL21 strains coexpressed with ferredoxin in absence of ADO (trace c), AtoB-TPC7 route engineered in *E. coli* BL21 strains (trace d) and control *E. coli* BL21 cells without pathway engineering (trace e) are shown.

BL21 (DE3) (fhuA2 [lon] ompT gal (λ DE3) [dcm] ΔhsdS) cells from Novagen were used for protein expression. The ahr (GenBank ID: ACT44688.1) and yqhD (Gen- Bank ID: AAA97166.1) single and double knockout strains were generated in a previous study [Kallio P et al. *Nature communications* 2014, 5:4731]. The structure of all plasmids is graphically depicted in FIG. 7 and their preparation is described herein.

pET-TPC7.

The pET-TPC7 plasmid was constructed in a pETDuetT-1 vector (ColE1 replicon, Ampicillin®, from Novagen) by replacing TE4 acyl-ACP thioesterase with a synthesized gene encoding YciA (*Haemophilus influenza*, GenBank ID: AAC22485.1) in pET-TPC4 backbone plasmid described in the previous study using restriction sites HindIII and NcoI [Kallio P et al. *Nature communications* 2014, 5:4731]. The final plasmid contained synthesized genes encoding Sfp (maturation factor phosphopantetheinyl transferase from *Bacillus subtilis*, GenBank ID: X65610.1), and CAR (carboxylic acid reductase from *Mycobacterium marinum*, GenBank ID: ACC40567.1) upstream to yciA.

pACYC-NHCT.

The pACYC-NHCT plasmid was constructed in a pACYCDuet-1 vector (P15A replicon, Chloramphenicol®, from Novagen) by subcloning a synthesized NcoI-BamHI gene fragment (GenScript, USA) carrying genes encoding NphT7 (acetoacetyl-CoA synthase from *Streptomyces* sp. CL190, GenBank ID: D7URV0.1) and Hbd (3-hydroxybutyryl-CoA dehydrogenase from *Clostridium acetobutylicum* ATCC 824, GenBank ID: P52041.2) into a synthesized pACYC construct harbouring crt (3-hydroxybutyryl-CoA dehydratase from *Clostridium acetobutylicum* ATCC 824, GenBank ID: P52046.1) and ter (trans-2-enoyl-CoA reductase from *Treponema denticola* ATCC 35405, GenBank ID: Q73Q47.1).

pACYC-AHCT.

pACYC-AHCT is a pACYCDuet-1 vector (P15A replicon, Chloramphenicol®, from Novagen) with atoB (acetyl-CoA acetyltransferase from *E. coli*, GenBank ID: P76461.1), hbd (3-hydroxybutyryl-CoA dehydrogenase from *Clostridium acetobutylicum* ATCC 824, GenBank ID: P52041.2), crt (3-hydroxybutyryl-CoA dehydratase from *Clostridium acetobutylicum* ATCC 824, GenBank ID: P52046.1) and ter (trans-2-enoyl-CoA reductase from *Treponema denticola* ATCC 35405, GenBank ID: Q73Q47.1) genes inserted in the order. Gene atoB (acetyl-CoA acetyltransferase from *E. coli*, GenBank ID: P76461.1) was PCR-amplified from *E. coli* K-12 purified genome, using primers 5'-attaggtaccAAAAATTGTGTCATCGTCA-GTGCGGTAC (SEQ ID NO: 1) and 5'-attaaagcTTAAT-TCAACCGTTCAATCACCATCGCAAT (SEQ ID NO:2), showing complementary regions in capital letters. The atoB PCR fragment was then subcloned into pACYC-NHCT, thus replacing the KpnI-HindIII fragment carrying NphT7, resulting pACYC-AHCT plasmid.

pET-AdhE2.

The pET-AdhE2 plasmid was constructed in a pET-Duet vector (f 1 origin, Ampicillin®, from Novagen) with adhE2 by subcloning synthesized gene encoding AdhE2 (aldehyde-alcohol dehydrogenase, from *Clostridium acetobutylicum* ATCC 824, GenBank ID: Q9ANR5) from a pUC57 parent vector provided by GenScript (USA) into pET-Duet vector, using restriction sites NcoI and AvrII.

pCDF-ADO and pCDF-ADO$_{A134F}$.

The pCDF-ADO plasmid was constructed in a pCDF-Duet-1 vector (CDF replicon, streptomycin/Spectinomycin®, from Novagen) with ADO (aldehyde deformylating oxygenase from *Prochlorococcus marinus* MIT9313, GenBank ID: Q7V6D4.1) cloned into the vector using NcoI and EcoRI restriction sites.

The pCDF-ADO$_{A134F}$ vector was created by mutating the ADO insert, using A134F_forward (5'-GCA TTT GCG ATT TCT TTT TAT CAT ACG TAC-3') (SEQ ID NO:3) and A134F_reverse primers (5'-GTA CGT ATG ATA AAA AGA AAT CGC AAA TGC-3') (SEQ ID NO:4). The correct mutations were confirmed by complete plasmid DNA sequencing. Gene encoding ADO was originally provided by E. Neil G. Marsh (Department of Biological Chemistry, University of Michigan, USA) in a pET28b-cAD vector which was used for the previous study [Eser B E et al. *Biochemistry-Us* 2011, 50:10743-10750].

pCDF-Ahr.

The pCDF-Ahr plasmid was constructed in a pCDF-Duet-1 vector (CDF replicon, streptomycin/Spectinomycin®, from Novagen). Gene encoding Ahr (aldehyde reductase from *E. coli* GenBank ID: P27250.2) was PCR-amplified from isolated *E. coli* K-12 genomic DNA, using primers 5' ATTAATCCATGGTCTAGATAATTAATG-GATCCAGGAGGAAACATATGTCGAT GATAAAAAGCTATGCCGCAAAAG-3' (SEQ ID NO:5) and 5'-ATTAATCCTAGGAAGCTTCTCGAGT-CAAAAATCGGCTTTCAACACCACGCGG-3' (SEQ ID NO:6), and cloned into using restriction sites NcoI and AvrII [Akhtar M K et al. *Proc Natl Acad Sci USA* 2013, 110:87-92].

pRSF-PetF.

The pRSF-PetF plasmid was constructed in a pRSF-Duet1 vector (RSF replicon, Kanamycin®, from Novagen) with fdx (ferredoxin from *Synechocystis* sp PCC 6803, GenBank ID: WP_010873424.1) by subcloning synthesized gene from a pUC57 parent vector provided by GenScript (USA) into a pRSF-Duet1 vector using NcoI and AvrII restriction sites.

Co-Expression and Introduction of the Pathway in *E. coli*

The atoB-adhE2 route was introduced into *E. coli* or the knockout cells by co-expressing pACYC-AHCT and pET-AdhE2 vectors. The atoB-TPC7 route was introduced into *E. coli* or the knockout cells by co-expressing pACYC-AHCT and pET-TPC7 vectors. The nphT7-adhE2 route was introduced into *E. coli* or the knockout cells by co expressing pACYC-NHCT and pET-AdhE2 vectors. The nphT7-TPC7 route was introduced into *E. coli* or the knockout cells by co-expressing pACYC-NHCT and pET-TPC7 vectors in the cells.

*E. coli* cells containing engineered pathways were further engineered by co-transforming either pCDF-ADO or pCDF-ADO$_{A134F}$ vectors in order to introduce ADO or the ADO$_{A134F}$ variant. The pRSF-PetF vector was co-expressed for Fdx, while pCDF-Ahr was used to introduce Ahr enzyme in the pathway. The presence of all the proteins in each individual plasmid was confirmed by SDS-PAGE and mass spectrometry analysis of the respective SDS-PAGE bands. In the case of proteins with a hexahistidine tag, Western blotting (using WesternBreeze Chemiluminescent Immunodetection kit from Invitrogen) was also used to analyse the expression of his-tagged proteins.

SDS-PAGE Analysis of Protein Expression in Cells Containing Plasmids Encoding Pathway Components Protein expression levels in cells containing plasmids that encode the pathway enzymes were examined by SDS-PAGE. T5 media (20 mL; 12 g tryptone, 24 g yeast extract, 4 mL glycerol, 12.5 g K$_2$HPO$_4$, 2.3 g KH$_2$PO$_4$, 20 g glucose per liter) was inoculated with 1% (v/v) transformed *E. coli* cells and incubated at 37° C. (180 rpm) until the optical density at 600 nm (O.D$_{600\ nm}$) reached 0.5. Cultures were then induced with isopropyl β-D-1-thiogalactopyranoside (IPTG; final concentration of 0.5 mM). Cultures were grown for a further 24 hours at 30° C. (180 rpm). Samples (200 µL) from the cultures were taken for SDS PAGE analysis. Samples were taken before IPTG induction and after 4 or 24 hours of IPTG induction and cells harvested by centrifugation. Samples were electrophoresed in 12% RunBlue precast SDS-PAGE gels (Expedeon, Cambridge, UK). Protein bands were visualized by staining with Instant Blue protein stain (Expedeon).

Media, Cultivation and Detection of Propane and Butanol

Lysogeny broth (LB) liquid media (10 mL) was inoculated using E. coli glycerol stocks (from −80° C.) and incubated at 37° C. overnight at 180 rpm. 50 mL of T5 media (12 g tryptone, 24 g yeast extract, 4 mL glycerol, 12.5 g $K_2HPO_4$, 2.3 g $KH_2PO_4$, 20 g glucose per liter) was inoculated with 1% (v/v) of the inoculum and kept for incubation at 37° C. (180 rpm) until the optical density at 600 nm ($O.D_{600}$) reached 0.5. The cultures were then induced with isopropyl β-D-1-thiogalactopyranoside (IPTG) to a final concentration of 0.5 mM. The cell cultures were further grown for 4 hours at 30° C. and 180 rpm to prepare the samples for propane detection. In the case of total butanol produced in the butanol pathway the culture was left at 30° C. (180 rpm) for 72 hours, while for residual butanol detection samples were taken from this culture when $O.D_{600}$ reached 1.5. Control cultures were made using untransformed E. coli strain BL21 DE3 cells. For propane formation analysis, 50 mL cell culture was centrifuged at 4000 rpm and the supernatant was discarded. The cell pellets were resuspended in a 6.25 mL T5 media with 0.5 mM IPTG and 500 µL of the resuspended culture was transferred into 2 mL crimp sealed GC vial and used for propane analysis. The vials were incubated at 30° C., with shaking at 180 rpm for 3 hrs. 1.0 mL headspace from the cultures grown in the GC vial was manually removed and injected into the GC with a gas tight syringe. Propane detection was carried out using a Varian 3800 GC equipped with a DB-WAX column (30 m×0.32 mm×0.25 µM film thickness, JW Scientific). The injector temperature was 250° C. with a split ratio of 10:1. The column temperature was set from 40° C. hold for 2 min to 100° C. at 20° C./min with helium flow at 1 mL/min and FID temperature at 250° C. Propane peak was identified by comparing it with the analytical propane standard and quantification was done using a propane calibration curve.

For residual butanol detection 50 mL liquid culture was spun down at 4000 rpm for 10 min. 500 µL of the supernatant was extracted with 500 µL of ethyl acetate containing 0.2% hexane as internal standard and dried over $MgSO_4$. 1 µL sample was analysed in GC using a Varian 3800 GC equipped with a HP-5 column (30 m×0.32 mm×0.25 µM film thickness, JW Scientific). The injector temperature was 250° C. with a split ratio of 20:1. The column temperature was set from 40° C. hold for 1 min to 280° C. at 20° C./min with helium flow at 1 mL/min and FID temperature at 250° C. Butanol peak was identified by comparing with the analytical butanol standard and quantification was done using a butanol calibration curve.

Example 2

Synthesis of Butyraldehyde Based on the CoA-Dependent 1-Butanol Pathway

Figure 2:
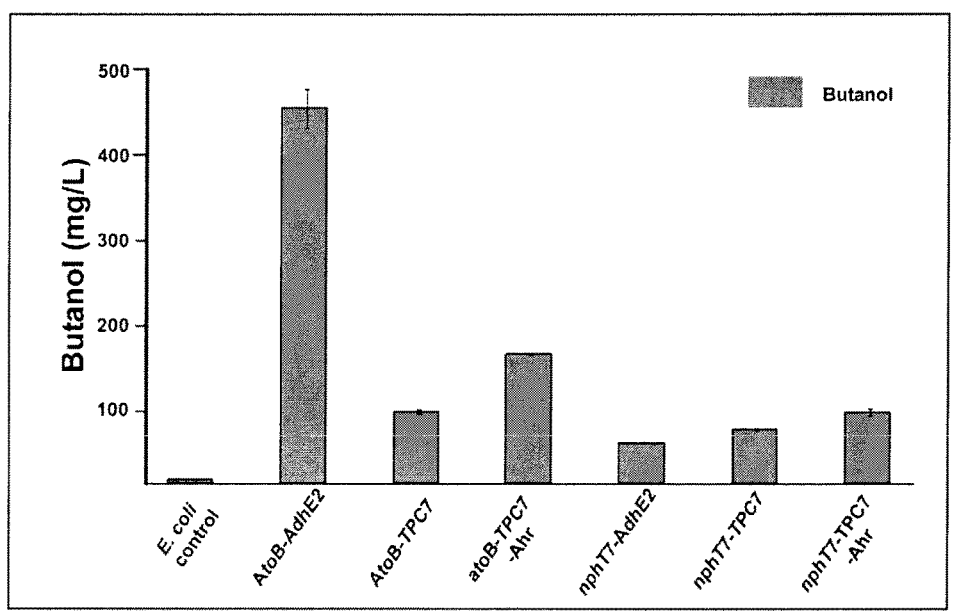
FIG. 2 depicts in accordance with various embodiments of the invention, total butanol produced by the engineered *E. coli* BL21 strains. Total butanol concentration obtained after 72 hours of cultivation of *E. coli* wild-type cells harbouring engineered constructs is shown. Error bars are standard deviation (n=4).
Figure 9:
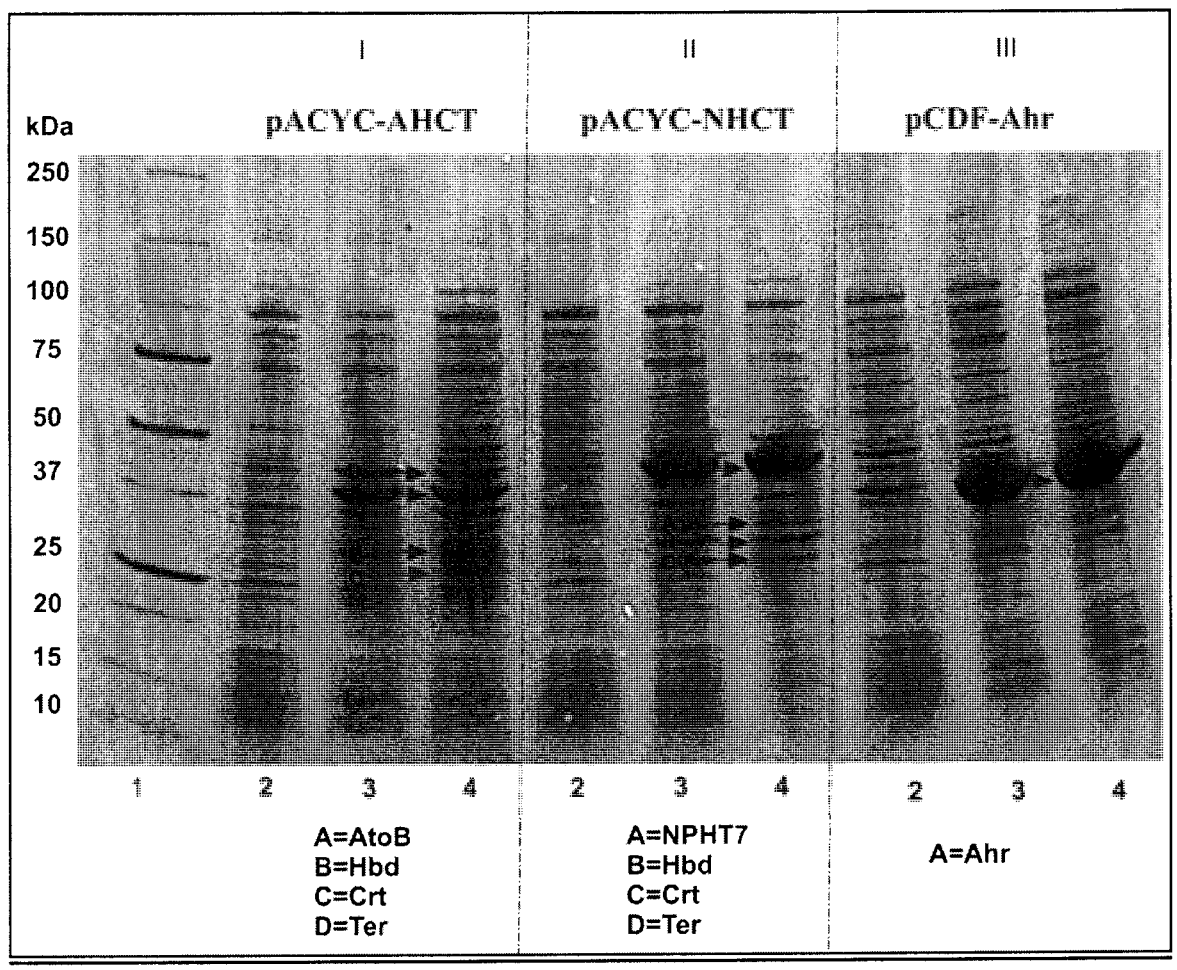
FIG. 9 depicts in accordance with various embodiments of the invention, SDS-PAGE analysis of overexpressed proteins in *E. coli* cells transformed with plasmids pACYC-AHCT, pACYC-NHCT and pCDF-Ahr. The SDS-PAGE gel shows IPTG uninduced and induced *E. coli* cells transformed with pACYC-AHCT, pACYC-NHCT and pCDF-Ahr vectors (sections I, II and III, respectively). Lane 1 is the standard protein marker and in each section, lane 2 shows uninduced cells, lane 3 shows IPTG induced cells after 4 hours and lane 4 is the IPTG induced cells after 24 hours. AtoB, acetyl-CoA acetyltransferase (molecular weight 40.5 kDa); NphT7, acetoacetyl CoA synthase (molecular weight 34.6 kDa); Hbd, 3-hydroxybutyryl-CoA dehydrogenase (molecular weight 30.6 kDa); Crt, 3-hydroxybutyryl-CoA dehydratase (molecular weight 28.2 kDa); Ter, trans-2-enoyl-CoA reductase (molecular weight 43.8 kDa) and Ahr, aldehyde reductase (molecular weight 37.8 kDa) enzymes are marked in the SDS-PAGE. The presence of all proteins expressed from each individual plasmid was confirmed by mass spectrometry analysis of the respective SDS-PAGE bands.
Figure 10:
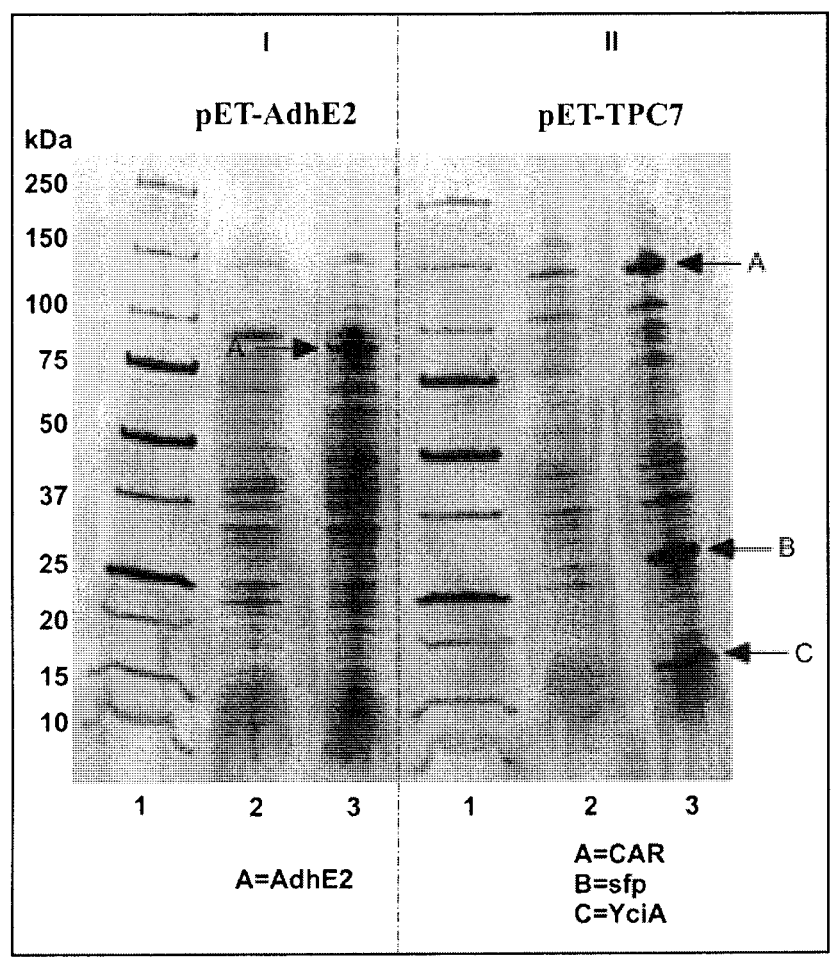
FIG. 10 depicts in accordance with various embodiments of the invention, SDS-PAGE analysis of overexpressed proteins in *E. coli* cells transformed with pET-adhE2 and pET-TPC7 vectors. The SDS-PAGE gel shows IPTG uninduced and induced *E. coli* cells transformed with pET-AdhE2 and pET-TPC7 vectors (shown in sections I and II, respectively). Lane 1 is the standard protein marker and in each section, lane 2 shows uninduced cells and lane 3 is the IPTG induced cells after 24 hours. The band positions of AdhE2, aldehyde-alcohol dehydrogenase (molecular weight 94.4 kDa); CAR, carboxylic acid reductase (molecular weight 128.9 kDa); sfp (maturation factor phosphopantetheinyl transferase) (molecular weight 26.2 kDa) and YciA, acyl-CoA thioester hydrolase (molecular weight 16.7 kDa) are shown. The presence of all proteins was confirmed by mass spectrometry analysis of the respective SDS-PAGE bands.
Figure 11:
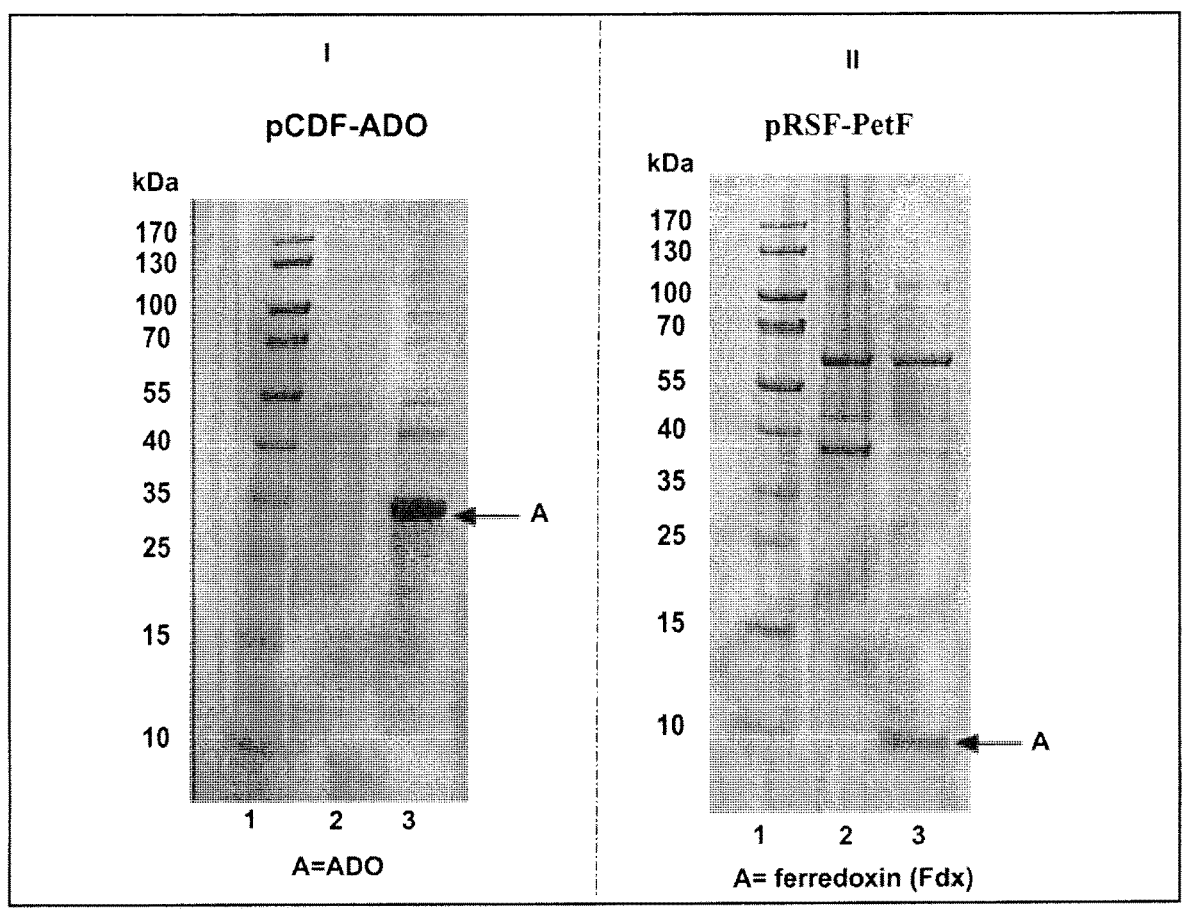
FIG. 11 depicts in accordance with various embodiments of the invention, SDS-PAGE analysis of overexpressed proteins in *E. coli* cells transformed with pCDF-ADO and pRSF-PetF vectors. The SDS-PAGE gel shows IPTG uninduced and induced *E. coli* cells transformed with pCDF-ADO and pRSF-PetF vectors (shown in sections I and II respectively). Lane 1 is the standard protein marker and in each section, lane 2 shows uninduced cells, and lane 3 is the IPTG induced cells after 24 hours. The positions of ADO, aldehyde deformylating oxygenase (molecular weight 29.3 kDa) and Fdx, ferredoxin (molecular weight 10.4 kDa) are shown. The presence of all proteins was confirmed by mass spectrometry analysis of the respective SDS-PAGE bands.

For propane production, the ADO enzyme requires butyraldehyde as a precursor. We therefore constructed two biosynthetic pathways for butyraldehyde synthesis based on the fermentation pathway of 1-butanol, as summarized in FIG. 1. The initial step of the pathway consisted of i) either AtoB from E. coli (FIG. 1; atoB route) or NphT7 from Streptomyces sp. (FIG. 1; nphT7 route) to convert the metabolic pathway intermediate, acetyl-CoA to acetoacetyl-CoA [Lan E I and Liao J C Metab Eng 2011, 13:353-36317; Shen C R et al. Appl Environ Microb 2011, 77:2905-2915]. Although the latter step has not previously been evaluated in E. coli, it was recently shown to be superior to AtoB for butanol production in Synechococcus elongatus PCC 7942 [Lan E I, Liao J C Proc Natl Acad Sci USA 2012, 109:6018-6023]. For the second and third steps, clostridial 3-hydroxybutyryl-CoA dehydrogenase (Hbd) and 3-hydroxybutyryl-CoA dehydratase (crotonase or Crt) were used to convert acetoacetyl-CoA to crotonyl-CoA. For the fourth step, the oxygen-sensitive flavoenzyme butyryl-CoA dehydrogenase, present in the native clostridial pathway, was replaced with NADH-dependent trans-enoyl-CoA reductase (Ter) from Treponema denticola to reduce crotonyl-CoA to butyryl-CoA [Shen C R et al. Appl Environ Microb 2011, 77:2905-2915]. In the final step, butyraldehyde was synthesised by NAD(P)H-dependent reduction of butryl CoA catalysed by AdhE2. To verify pathway functionality for butyraldehyde synthesis, we used butanol as a molecular reporter since numerous studies have shown that it can be stably accumulated in E. coli and easily monitored [Pasztor A, et al. Biotechnology and bioengineering 2014]. Expressions of all pathway components were confirmed by SDS-PAGE (FIGS. 9-11) and pathway functionality was verified by mass spectrometry. Both routes led to the production of 1-butanol clearly indicating that both pathways were capable of butyraldehyde synthesis. The strain harbouring the atoB route led to a 6.2 fold higher production of 1-butanol production (473.3±3.2 mg/L) compared to the nphT7 route (FIG. 2).

Example 3

Modification of the Butyraldehyde Pathway by Replacement of AdhE2

In the clostridial pathway, butyryl-CoA is converted to butanol in two successive catalytic steps by the bifunctional aldehyde/alcohol dehydrogenase AdhE2 (FIG. 1; AdhE2 route) [Fontaine L et al. J Bacteriol 2002, 184:821-830]. From an engineering perspective, this is highly undesirable since the local presence of an aldehyde reductase component of AdhE2 is likely to compete for the ADO substrate. Given this possibility and to avoid creating internal metabolic competition, we therefore replaced AdhE2 with a i) thioesterase (YciA) from Haemophilus influenzae to cleave butyryl-CoA to butyric acid and ii) ATP/NADPH-dependent carboxylic acid reductase (CAR) from Mycobacterium marinum to convert butyric acid to butyraldehyde [Akhtar M K et al. Proc Natl Acad Sci USA 2013, 110:87-92; Zhuang Z H, et al. Biochemistry-Us 2008, 47:2789-2796]. Two variant routes were thus created based on this modification, namely atoB-TPC7, atoB-TPC7-ahr, nphT7-TPC7 and nphT7-TPC7-ahr (FIG. 1; TPC7 route).

As before, 1-butanol was monitored to verify the functionality of the parts for butyraldehyde synthesis. In both cases, 1-butanol production was observed signifying yet again that butyraldehyde synthesis was achievable with both routes. 1-butanol production was increased with the atoB-TPC7 and nphT7-TPC7 routes when Ahr was over-expressed (1.5 and 1.3 times for atoB-TPC7 and nphT7-TPC7 routes respectively), indicating that the conversion of butraldehyde to butanol by the endogenous aldehyde reductases was limiting total pathway flux.

Example 4

Evaluation of Pathway Routes for Propane Synthesis

Figure 3:
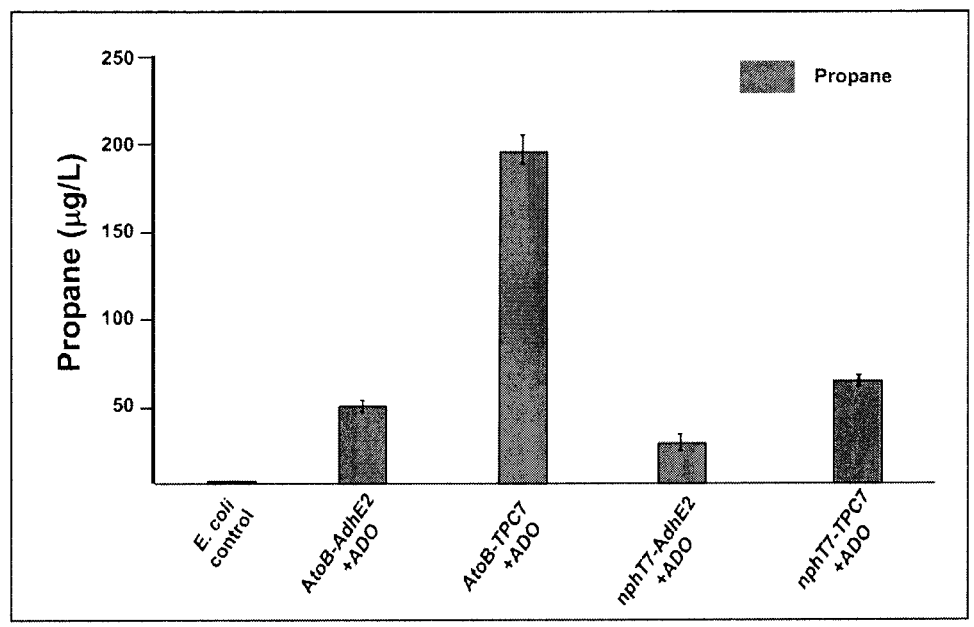
FIG. 3 depicts in accordance with various embodiments of the invention, Total propane produced by the engineered *E. coli* BL21 strains. Total propane accumulated over 4 hours of reaction under assay conditions performed in gas chromatography (GC) vials for the pathway-engineered *E. coli* cells, after overexpressing with ADO. Error bars are standard deviation (n=4).

The combined analysis clearly indicated that all pathway components for butyraldehyde synthesis were functional. In order to convert butyraldehyde to propane, the aldehyde reductases in the four butanol pathways were thereafter replaced or complemented by ADO. The TPC7-based strains produced relatively more propane (atoB-TPC7-ADO and nphT7-TPC7-ADO) compared to other strains (FIG. 3, 12-13) Interestingly, the lower amount of propane produced with the two AdhE2 pathways clearly supported our initial hypothesis regarding internal metabolic competition with AdhE2.

Figure 4:
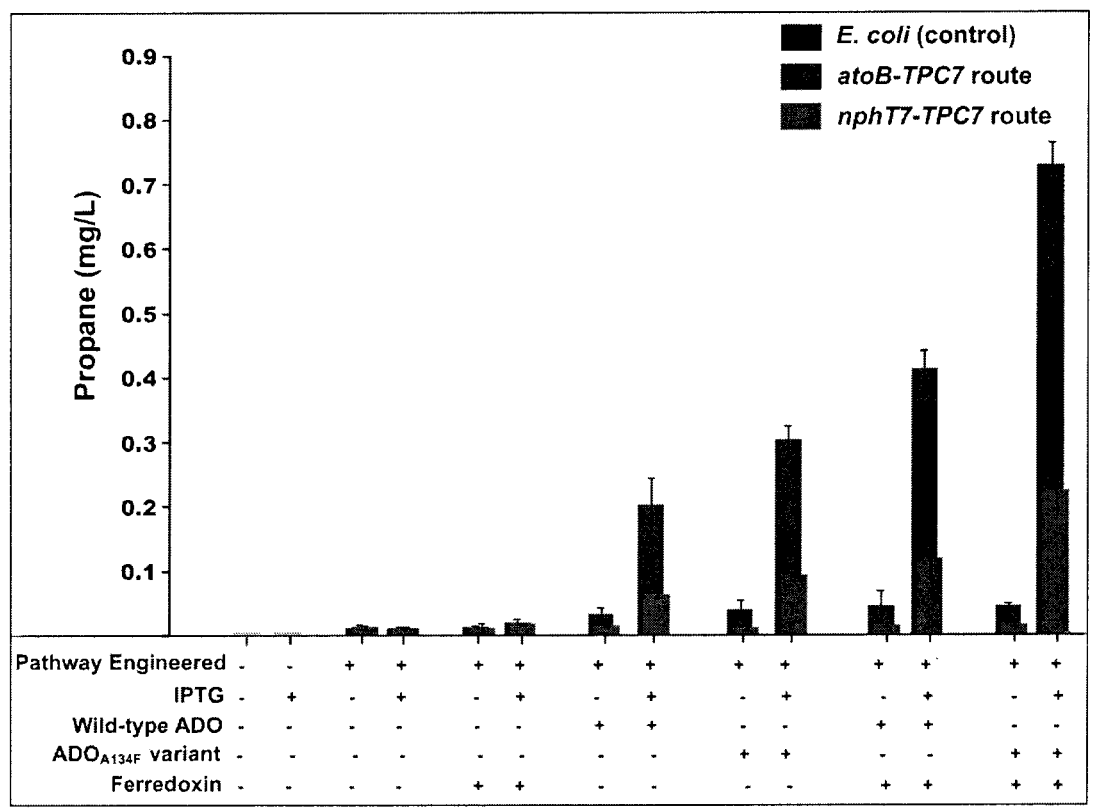
FIG. 4 depicts in accordance with various embodiments of the invention, propane production in pathway-engineered *E. coli* strains containing wild-type ADO or the ADO$_{A134F}$ variant enzyme. *E. coli* cells were either pathway-engineered to include the atoB-TPC7 route (indicated by red colour) or the nphT7-TPC7 route (indicated by green colour) and contain either wild-type ADO or the $ADO_{A134F}$ variant enzyme in the absence/presence of ferredoxin (Fdx) from *Synechocystis* sp PCC 6803. A detailed protocol for the pathway engineering and propane detection is included in Example 1 and FIG. 8.

The two functional TPC7-dependent propane pathways were subsequently further modified by replacing ADO with the $ADO_{A134F}$ variant enzyme (FIG. 4). This enzyme was initially designed to overcome some of the kinetic constraints in propane production resulting from very low activity of the enzyme towards short-chain substrates [Khara B et al. *Chembiochem* 2013, 14:1204-1208]. The A134F substitution alters the topology of the substrate-access channel, and has been shown to result in improved activity towards low chain-length aldehydes butyraldehyde and pentaldehyde. The $ADO_{A134F}$ has also been shown to generate propane in both in vitro and in vivo biotransformations, and the *E. coli* strain expressing the variant enzyme produced approximately two times more propane (0.47±0.04 mg/L) in comparison to the corresponding wild-type ADO system when fed with externally added butyraldehyde [Khara B et al. *Chembiochem* 2013, 14: 1204-1208]. As expected, introduction of the variant ADO into the pathways engineered in this study also resulted in enhanced propane production in all cases (FIG. 4). The best result was obtained with the atoB-TPC7-$ADO_{A134F}$ combination, showing a 1.8 fold improvement, in comparison to the wild-type ADO system, and reaching a maximum propane titre of 0.29±0.02 mg/L (FIG. 4).

Example 5

Increasing Electron Supply to ADO Via Ferredoxin

Figure 12:
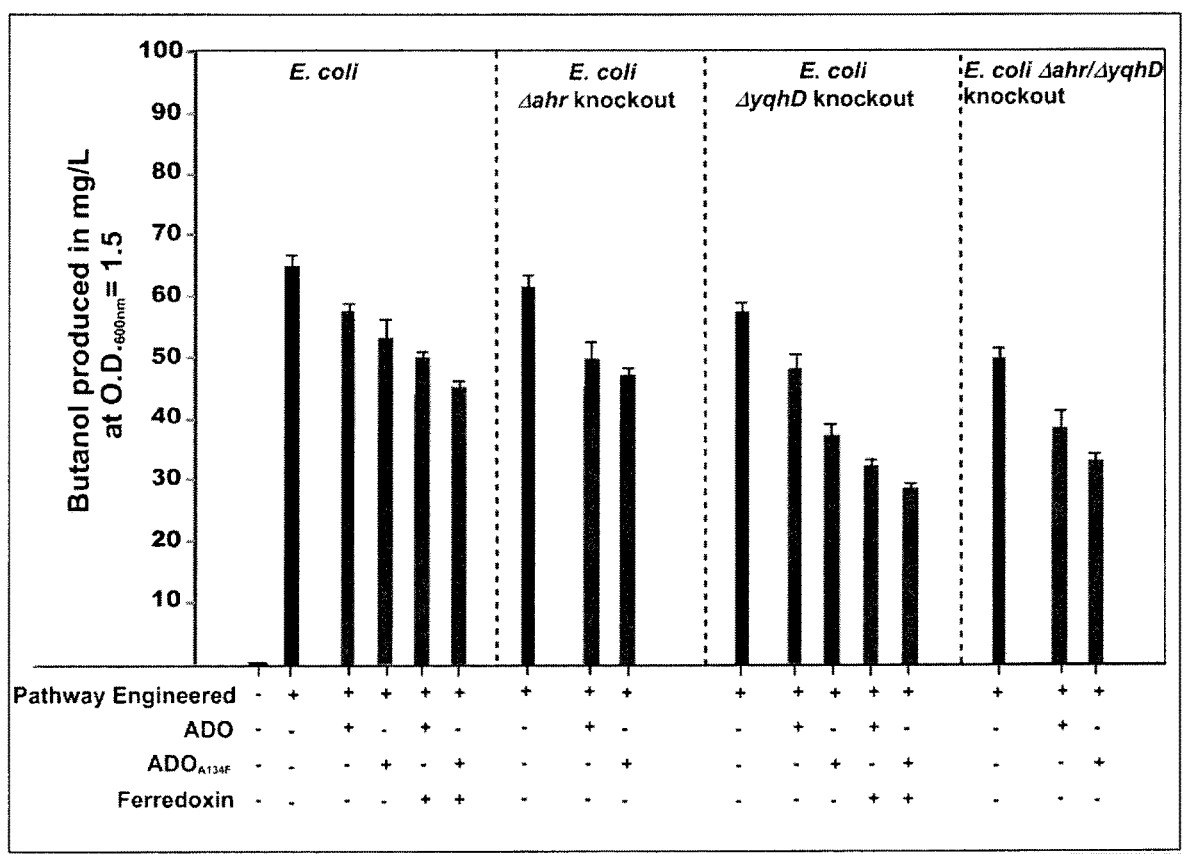
FIG. 12 depicts in accordance with various embodiments of the invention, Residual butanol produced in *E. coli* and knockout strains engineered to harbour the atoB-TPC7 pathway. Residual butanol produced in the pathway engineered *E. coli* or knockout strains with wild-type ADO or with the $ADO_{A134F}$ variant enzyme are shown. *E. coli* and Δahr/ΔyqhD single or double knockout strains were engineered to contain the atoB-TPC7 route (indicated by red colour). The effect of wild-type ADO or the $ADO_{A134F}$ variant enzyme with or without *Synechocystis* ferredoxin (Fdx) was also analysed. Detailed protocols for the pathway engineering and residual butanol detection are included in the Materials and Methods section (main manuscript). Error bars are standard deviation (n=4).
Figure 13:
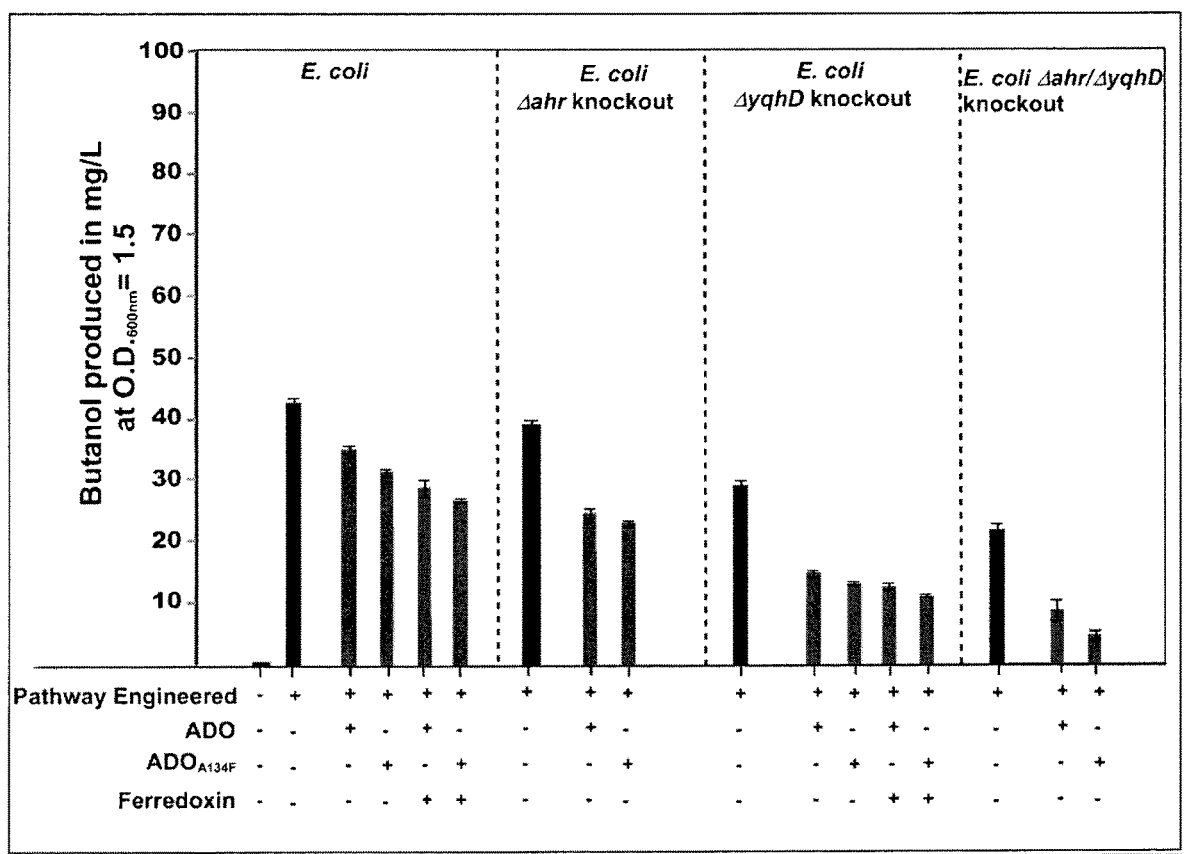
FIG. 13 depicts in accordance with various embodiments of the invention, Residual butanol produced in *E. coli* and knockout strains engineered to harbour the nphT7-TPC7 pathway. Residual butanol produced in the pathway engineered *E. coli* or knockout strains with wild-type ADO or with the $ADO_{A134F}$ variant enzyme are shown. *E. coli* and Δahr/ΔyqhD single or double knockout strains were engineered to contain the nphT7-TPC7 route (indicated by green colour). The effect of wild-type ADO or the $ADO_{A134F}$ variant enzyme with or without *Synechocystis* ferredoxin (Fdx) was also analysed. Detailed protocols for the pathway engineering and residual butanol detection are included in the Materials and Methods section (main manuscript). Error bars are standard deviation (n=4).

It has previously been shown that the supply of electrons to ADO via endogenous enzymes was inadequate for effective alkane biosynthesis in *E. coli* [Kallio P et al. *Nature communications* 2014, 5:4731]. To alleviate this constraint, the heterologous ferredoxin PetF (ssl0020), the presumed natural electron acceptor/donor to ADO in *Synechocystis* sp. PCC 6803, was over-expressed as part of the engineered pathways. Consequently, co-expression of PetF improved propane production by roughly two-fold for both the atoB-TPC7 and nphT7-TPC7 pathway in combination with both ADO and $ADO_{A134F}$ (FIG. 4). In order to verify the impact of the optimization efforts, residual butanol was also measured in selected strains (FIGS. 12 and 13). If ADO was able to compete for butyraldehyde, the common precursor for both propane and butanol, one would expect to observe a lower butanol titre in strains with enhanced propane production. Indeed, residual butanol levels were decreased when ADO and ferredoxin were overexpressed. Similarly, when the $ADO_{A134F}$ variant replaced wild-type ADO, the accumulation of butanol in the media was also lower. This is consistent with the terminal ADO (and the $ADO_{A134F}$ variant) acting on butyraldehyde produced by the engineered synthetic pathway (FIGS. 12 and 13).

Example 6

Removing Competing Pathways for Propane Synthesis

Figure 5A:
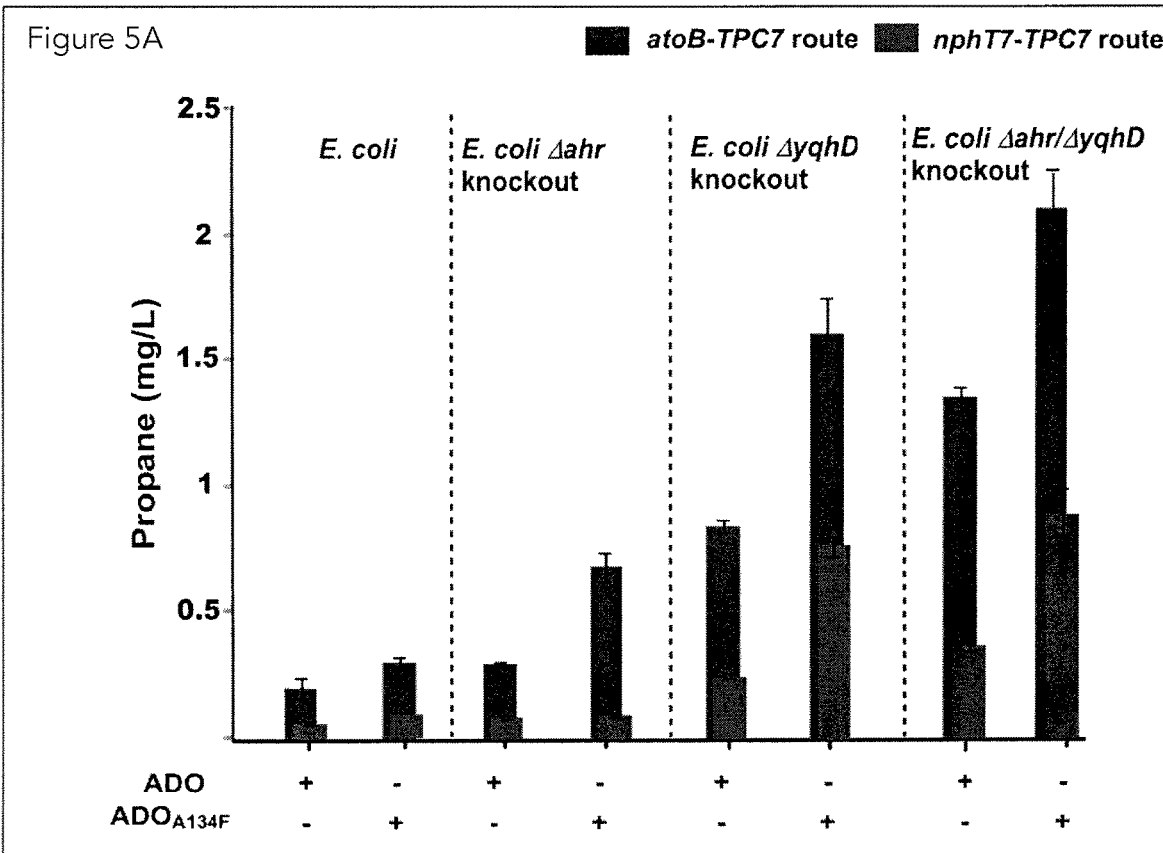
FIGS. 5A and 5B depict in accordance with various embodiments of the invention, propane produced in pathway-engineered Δahr/ΔyqhD single or double knockout *E. coli* strains and the effects of co-expressing a ferredoxin electron donating system. Propane production in the pathway engineered ΔyqhD knockout cells with wild-type ADO or with the $ADO_{A134F}$ variant enzyme is shown (FIG. 5A). The ΔyqhD knockout strains were either engineered to contain the atoB-TPC7 route (indicated by red colour) or the nphT7-TPC7 route (indicated by green colour). Wild-type ADO or the $ADO_{A134F}$ variant enzyme was co-expressed in the engineered cells either in combination with or without ferredoxin (Fdx) from *Synechocystis* sp PCC 6803 (FIG. 5B). A detailed protocol for the pathway engineering and propane detection is included in Example 1 and FIG. 8. Error bars are standard deviation (n=4).
Figure 5B:
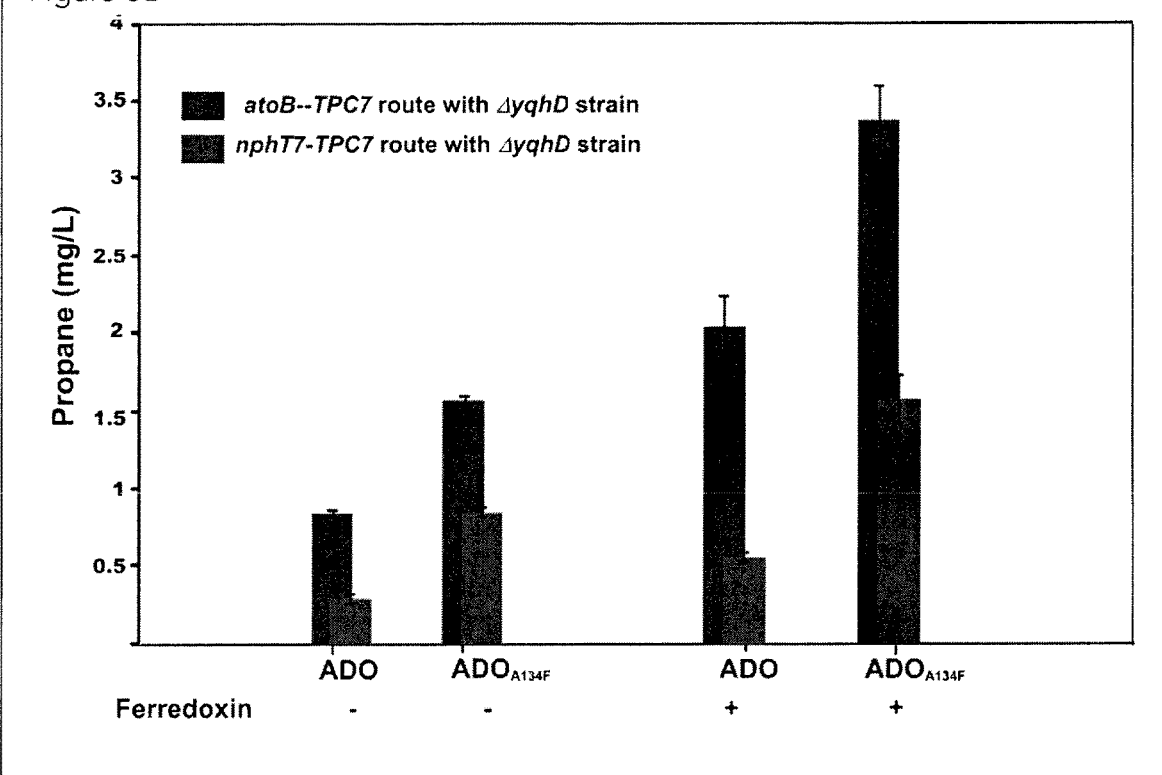

*E. coli* cells contain a wide range of aldehyde reductases and alcohol dehydrogenases which act to scavenge potentially toxic intracellular aldehydes [Rodriguez G M, Atsumi S: *Metab Eng* 2014, 25:227-237]. Two of the native aldehyde reductases in *E. coli*, Ahr and YqhD, were previously shown to compete for butyraldehyde [Kallio P et al. *Nature communications* 2014, 5:4731]. In order to further optimize propane production, Δahr and ΔyqhD single and double knockout *E. coli* strains were therefore tested (FIG. 5A). Among the single knockout strains, ΔyqhD showed a greater increase in propane production compared to Δahr. The double knockout strain Δahr/ΔyqhD showed a cumulative effect of the gene knockouts, reaching a propane titre of 2.05±0.12 mg/L for the atoB-TPC7-$ADO_{A134F}$ strain. The single knockout strains were also tested for propane production in the presence of *Synechocystis* sp ferredoxin (Fdx), reaching a titre of up to 3.40±0.19 mg/L in the ΔyqhD background (FIG. 5B).

Example 7

Potential for Large-Scale Production of Propane

Figure 6:
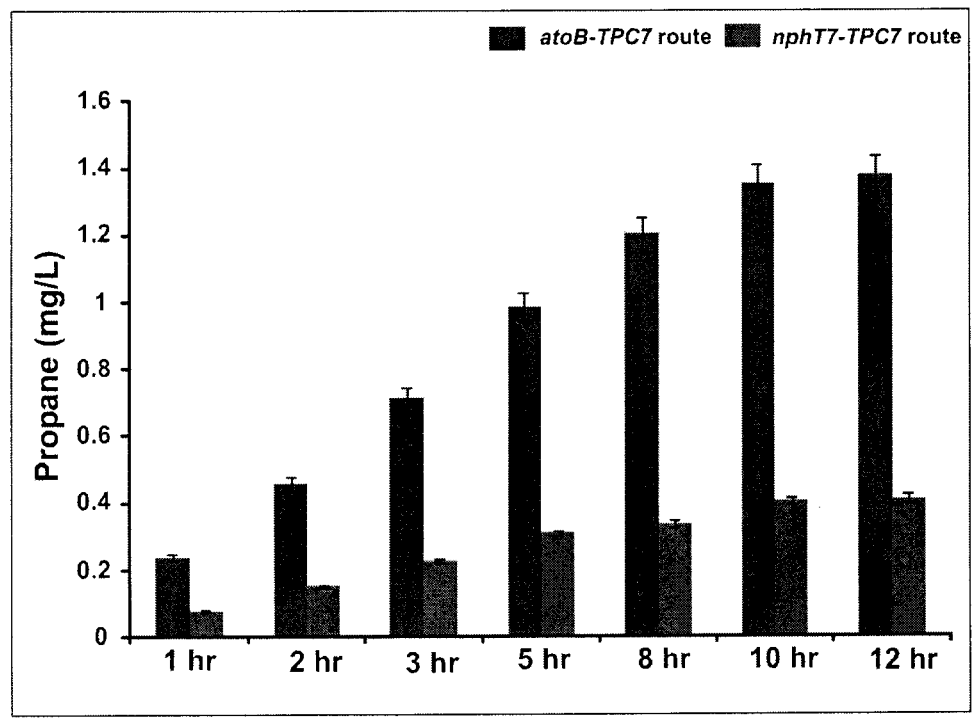
FIG. 6 depicts in accordance with various embodiments of the invention, larger scale cultures of the best performing propane-producing pathways. The atoB-TPC7 route (indicated by red colour) and nphT7-TPC7 (indicated by green colour) engineered in ΔyqhD knockout cells in the presence of the $ADO_{A134F}$ variant and ferredoxin system were analysed at larger scale. The culture volume was scaled up 400-fold to 200 mL, in a 300 mL flask sealed with airtight rubber septum. The propane accumulation for 12 hours is shown. Error bars are standard deviation (n=3).
Figure 14:
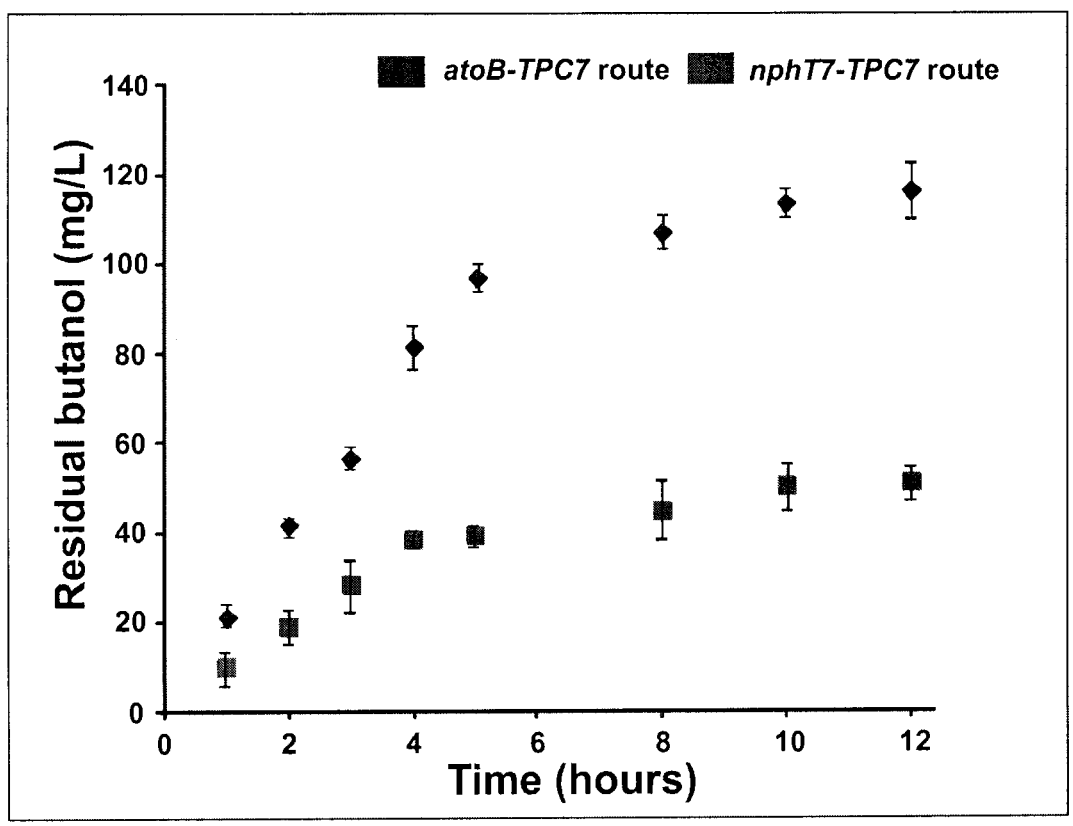
FIG. 14 depicts in accordance with various embodiments of the invention, Time course for residual butanol accumulation in large-scale cultures of the best propane-producing pathways. The atoB-TPC7 route (indicated by red symbols) and nphT7-TPC7 (indicated by green symbols) engineered in ΔyqhD knockout cells in the presence of the $ADO_{A134F}$ variant and ferredoxin system were analysed at larger scale. The culture volume was scaled up 400-fold to 200 mL, in a 300 mL flask sealed with airtight rubber septum. The residual butanol in the cultures for 12 hours is shown. Error bars are standard deviation (n=3).

As propane biosynthesis was only analysed in small-scale cultures (2.0 mL GC vials), larger scale productivity and longevity of propane production was also investigated with the best performing strains (i.e. atoB-TPC7 or nphT7-TPC7 routes incorporated into *E. coli* ΔyqhD in the presence of the $ADO_{A134F}$ variant and ferredoxin). The culture volume was scaled 400-fold to 200 mL, in 300 mL flasks sealed with air-tight rubber septa, and propane production and accumulated residual butanol were monitored over 12 hours (FIGS. 6 and 14). The highest propane accumulation was observed between 8-10 hours. For the atoB-TPC7 route, 1.38±0.06 mg/L propane was accumulated within 12 hours, while 0.4±0.1 mg/L propane was accumulated for the nphT7-TPC7 pathway (FIG. 6). The ability to scale propane production is an important proof-of-concept that suggests large-scale propane production should be possible in a fermentor set-up with appropriate optimisation of growth and feeding conditions. Controlled cultivation in a fermentor should bypass potential problems associated with flask cultivation e.g. non-optimal oxygen supply and the production of undesirable byproducts.

Recent progress in exploring various heterologous microbial platforms towards metabolites such as fatty acids, alcohols and alkanes has improved the prospect of advanced biofuel production. Propane ($C_3H_8$) was proposed as a new microbial biofuel target as it would be able to act as a direct drop-in replacement for the corresponding non-renewable products currently in use (e.g. autogas, LPG). Propane also has very good physicochemical properties which allow it to be stored and transported in a compressed liquid form, while under ambient conditions it is a clean-burning gas used in various applications ranging from heating to utilization as a transport fuel. The very first microbial biosynthetic pathway for producing propane was recently engineered in *E. coli* [Kallio P et al. *Nature communications* 2014, 5:4731]. In that study, it was found that the biosynthesis of propane was restricted by the poor activity of the enzyme ADO towards short-chain substrates in combination with competing pathways that limits the availability of the ADO substrate, butyraldehyde. Herein, the inventors therefore explored alternative biosynthetic approaches to provide a more comprehensive understanding of the limiting factors in microbial propane biosynthesis, and to find possible ways to overcome metabolic bottlenecks.

The pathways assembled in the present study are not dependent on type II fatty acid biosynthesis unlike in the previous study, and instead use CoA- rather than ACP-based intermediates. Importantly, this strategy allowed us to bypass the strict regulatory control on native fatty acid biosynthesis flux [Kallio P et al. *Nature communications* 2014, 5:4731; Davis M S, Cronan J E *J Bacteriol* 2001, 183:1499-1503; James E S, Cronan J E *J Biol Chem* 2004, 279:2520-2527]. The pathways engineered herein comprise four parallel variations of the Clostridial butanol pathway, differing from one another in the conversion of (1) acetyl-CoA to acetoacetyl-CoA (atoB vs. nphT7 routes) and (2) butyryl-CoA to butyraldehyde (adhE2 vs, TPC7 routes). In the first stage of pathway evaluation, production of butanol was used as a measure of metabolic flux towards butyraldehyde, the immediate substrate for propane production by ADO. The TPC7 variant routes were developed in order to avoid the bifunctional activity of AdhE2 which includes the reduction of butyraldehyde to 1-butanol. Such a reaction would be expected to compete with ADO for the butyraldehyde intermediate and lower propane production. Therefore, in order to separate these functional activities and allow greater pathway flexibility, AdhE2 was replaced with a 'TPC7' module in combination with Ahr.

For the first two variant pathways, the (co)substrate requirements for AtoB and NphT7 are quite distinct; AtoB requires two molecules of acetyl CoA whereas nphT7 requires acetyl-CoA along with malonyl-CoA. Both reactions result in the release of CoA though in the latter case there is also release of $CO_2$. The greater 1-butanol levels observed with the AtoB pathway suggest that it is a preferred route for acetoacetyl CoA production in *E. coli*. However it is also important to note that AtoB has a higher protein expression level in *E. coli* compared to nphT7 (FIG. 9) and this may have limited 1-butanol production via the nphT7 route. When coupled with ADO, butyraldehyde is converted to propane instead of butanol, and propane production was observed in the majority of the alternative strains. Consequently, the most productive propane pathway in the wild-type *E. coli* cells was observed with the atoB-TPC7-ADO route (220±3 µg/L). The flux towards propane through these pathways was compromised by competing native aldehyde reductase activities, as demonstrated by a significant increase in propane production and a concomitant reduction in butanol production following the deletion of two native genes encoding for such activities. In contrast to the two TPC7 pathways, the adhE2 dependent routes produced significantly less propane. This observation reinforced the view that AdhE2 converts butyraldehyde to butanol in successive steps without release of the butyraldehyde, thus preventing efficient interception of the pathway by ADO towards propane.

Quantitative comparisons revealed a difference of almost three orders of magnitude between the titres of butanol and propane (173 mg/L vs 0.2 mg/L) in the wild-type strains of AtoB-TPC7-Ahr and AtoB-TPC7-ADO. This difference can be attributed partly to the poor efficiency of the last biosynthetic step (conversion of butyraldehyde to propane). This is consistent with the earlier reports that have demonstrated in vitro and in vivo in *E. coli* that ADO has very low activity even towards the most preferred native substrates (C10-C15), and especially towards C4 substrates. To partially alleviate this constraint, the $ADO_{A143F}$ variant was introduced into the engineered pathways to replace native ADO. This resulted in a 1.8 fold improvement in propane, most likely reflecting more efficient utilization of the intracellular pool of available butyraldehyde. Furthermore, as confirmed herein, the reduction of ADO in the presence of a 2Fe-2S ferredoxin improves the metabolic reactions by mediating electron transfer in partner enzymes as observed herein.

The inventors' work introduces an alternative and conceptually different pathway for propane production in comparison to the previous work [Kallio P et al. *Nature communications* 2014, 5:4731] without the disadvantage of reliance on the FAS pathway, and which is appropriate for viable yet renewable mass-production of this key industrial chemical.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A genetically engineered bacterium, which expresses both an enzyme for butyraldehyde synthesis and a heterologous polypeptide having aldehyde deformylating oxygenase activity and produces propane from butyraldehyde as a precursor independent of fatty acid synthesis pathways.

2. The genetically engineered bacterium of claim 1, which further produces butanol.

3. The genetically engineered bacterium of claim 1, wherein propane is produced independent of aldehyde-alcohol dehydrogenase (AdhE2).

4. The genetically engineered bacterium of claim 1, comprising a deletion of aldehyde reductase (Δahr) enzyme, alcohol dehydrogenase (ΔyqhD) enzyme or a combination thereof.

5. The genetically engineered bacterium of claim 4, wherein the bacterium has been transformed with a first plasmid vector comprising a first nucleotide sequence encoding a polypeptide having acetyl-CoA acetyltransferase (AtoB) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

6. The genetically engineered bacterium of claim 5, wherein the bacterium has been co-transformed with a second plasmid vector selected from the group consisting of:
 a second plasmid vector comprising a first nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity; and
 a second plasmid vector comprising a nucleotide sequence encoding a polypeptide having aldehyde-alcohol dehydrogenase (AdhE2) activity.

7. The genetically engineered bacterium of claim 1, wherein the bacterium has been transformed with a first plasmid vector comprising a first nucleotide sequence encoding a polypeptide having acetyl-CoA acetyltransferase (AtoB) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

8. The genetically engineered bacterium of claim 7, wherein the bacterium has been co-transformed with a second plasmid vector selected from the group consisting of:
 a second plasmid vector comprising a nucleotide sequence encoding a polypeptide having aldehyde-alcohol dehydrogenase (AdhE2) activity; and
 a second plasmid vector comprising a nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity.

9. The genetically engineered bacterium of claim 1, wherein the bacterium has been transformed with a first plasmid vector comprising a first nucleotide sequence encoding a polypeptide having acetoacetyl-CoA synthase (NphT7) activity, a second nucleotide sequence encoding a polypeptide having 3-hydroxybutyrl-CoA dehydrogenase (Hbd) activity, a third nucleotide sequence encoding a polypeptide having 3-hydroxybutyryl-CoA dehydratase (Crt) activity and a fourth nucleotide sequence encoding a polypeptide having trans-2-enoyl-CoA reductase (Ter) activity.

10. The genetically engineered bacterium of claim 9, wherein the bacterium has been transformed with a second plasmid vector selected from the group consisting of:
- a second plasmid vector comprising a nucleotide sequence encoding a polypeptide having aldehyde-alcohol dehydrogenase (AdhE2) activity; and
- a second plasmid vector comprising a nucleotide sequence encoding a polypeptide having acyl-CoA thioester hydrolase (YciA) activity, a second nucleotide sequence encoding a polypeptide having the activity of a maturation factor for phosphopantetheinyl transferase (Sfp) and a third nucleotide sequence encoding a polypeptide having carboxylic acid reductase (CAR) activity.

11. The genetically engineered bacterium of claim 9, wherein the bacterium has been co-transformed with a second plasmid vector selected from the group consisting of:
- a second plasmid vector comprising a first nucleotide sequence encoding a polypeptide having acyl-CoA thioester hydrolase (YciA) activity, a second nucleotide sequence encoding a polypeptide having activity of a maturation factor for phosphopantetheinyl transferase (Sfp) and a third nucleotide sequence encoding a polypeptide having carboxylic acid reductase (Car) activity; and
- a second plasmid vector comprising a nucleotide sequence encoding a polypeptide having aldehyde-alcohol dehydrogenase (AdhE2) activity.

12. The genetically engineered bacterium of claim 11 wherein the bacterium has been co-transformed with a third plasmid vector comprising a nucleotide sequence encoding a polypeptide having aldehyde deformylating oxygenase (ADO) activity.

13. The genetically engineered bacterium of claim 11, wherein the bacterium has been co-transformed with a third plasmid vector comprising a nucleotide sequence encoding a polypeptide having aldehyde deformylating oxygenase activity wherein alanine at position 134 is substituted with phenylalanine ($ADOA_{134}F$).

14. The genetically engineered bacterium of claim 12, wherein the bacterium further comprises a polynucleotide encoding one or more ferredoxins so as to increase supply of electrons.

15. The genetically engineered bacterium of claim 14, the ferredoxin is PetF (ssl0020).

16. The genetically engineered bacterium of claim 1 which further expresses:
   (i) a heterologous polypeptide having acetyl-CoA acetyltransferase activity;
   (ii) a heterologous polypeptide having 3-hydroxybutyrl-CoA dehydrogenase activity;
   (iii) a heterologous polypeptide having 3-hydroxybutyryl-CoA dehydratase activity;
   (iv) a heterologous polypeptide having trans-2-enoyl-CoA reductase activity; and
   (v) a heterologous polypeptide having aldehyde-alcohol dehydrogenase activity.

17. The genetically engineered bacterium of claim 1 which further expresses:
   (i) a heterologous polypeptide having acetyl-CoA acetyltransferase activity;
   (ii) a heterologous polypeptide having 3-hydroxybutyrl-CoA dehydrogenase activity;
   (iii) a heterologous polypeptide having 3-hydroxybutyryl-CoA dehydratase activity;
   (iv) a heterologous polypeptide having trans-2-enoyl-CoA reductase activity;
   (v) a heterologous polypeptide having acyl-CoA thioester hydrolase activity;
   (vi) a heterologous polypeptide having the activity of a maturation factor for phosphopantetheinyl transferase; and
   (vii) a heterologous polypeptide having carboxylic acid reductase activity.

18. The genetically engineered bacterium of claim 1, wherein the enzyme for butyraldehyde synthesis is endogenously expressed.

19. A method for producing propane comprising:
   providing the genetically engineered bacterium of claim 1; and
   culturing the bacterium, so as to produce propane.

20. A method for producing butanol comprising:
   providing the genetically engineered bacterium of claim 2; and
   culturing the bacterium, so as to produce butanol.

* * * * *